US007563734B2

(12) United States Patent
Gleason et al.

(10) Patent No.: US 7,563,734 B2
(45) Date of Patent: Jul. 21, 2009

(54) CHEMICAL VAPOR DEPOSITION OF ANTIMICROBIAL POLYMER COATINGS

(75) Inventors: Karen K. Gleason, Lexington, MA (US); Tyler Phillip Martin, Quincy, MA (US); Kelvin Chan, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 323 days.

(21) Appl. No.: 11/103,360

(22) Filed: Apr. 11, 2005

(65) Prior Publication Data

US 2006/0228966 A1 Oct. 12, 2006

(51) Int. Cl.
B32B 27/04 (2006.01)
A61F 13/00 (2006.01)
A61L 15/00 (2006.01)

(52) U.S. Cl. .................. 442/123; 424/443; 424/445; 424/446; 424/447

(58) Field of Classification Search .................. 442/123
See application file for complete search history.

(56) References Cited

U.S. PATENT DOCUMENTS

| 5,407,581 | A * | 4/1995 | Onodera et al. ............. 210/654 |
| 6,790,910 | B1 | 9/2004 | Sosna et al. |
| 2003/0138645 | A1 | 7/2003 | Gleason et al. |

FOREIGN PATENT DOCUMENTS

EP 1192959 A 4/2002

OTHER PUBLICATIONS

Abel, Tanya, et al., "Preparation and investigation of antibacterial carbohydrate-based surfaces", *Carbohydrate Research*, 2002, 337, pp. 2495-2499.
Anguige, K. et al., "Mathematical modelling of therapies targeted at bacterial quorum sensing", *Math. Biosci.*, 2004, 192, pp. 39-83.
Baveja, J.K., et al., "Biological performance of a novel synthetic furanone-based antimicrobial", *Biomaterials*, 2004, 25, pp. 5013-5021.
Borman, Stu, "Surfaces Designed to Kill Bacteria", *Chemical and Engineering News*, 2002, 80, p. 36.
Chan, C. K., et al., "Acute Leukopenia as an Allergic Reaction to Silver Sulfadiazine in Burn Patients", *J. Trauma-Injury Infect. Crit. Care*, 1976, 16, pp. 395-396.
Chen, Y., et al., Biocidal Polystyrene Beads. III. Comparison of *N*-halamine and Quat Functional Groups, *Journal of Applied Polymer Science*, 2004, 92, pp. 363-367.
Chuanchuen, Rungtip, et al., Cross-Resistance between Triclosan and Antibiotics in *Pseudomonas aeruginosa* Is Mediated by Multidrug Efflux Pumps: Exposure of a Susceptible Mutant Strain to Triclosan Selects *nfxB* Mutants Overexpressing MexCD-OprJ, *Antimicrob. Agents Chemother.*, 2001, 45, pp. 428-432.
Donlan, Rodney M., et al.; "Biofilms: Survival Mechanisms of Clinically Relevant Microorganisms," *Clinical Microbiology Reviews*, 2002, 15, p. 167-193.
El Ola, Samiha Mohamed Abo, et al.; Unusual polymerization of 3-(trimethoxysilyl)-propyldimethyloctadecyl ammonium chloride on PET substrates, *Polymer*, 2004, 45, pp. 3215-3225.
Friedrich, C.L. et al.; "Antibacterial Action of Structurally Diverse Cationic Peptides on Gram-Positive Bacteria," *Antimicrob. Agents Chemother.* 2000, 44, pp. 2086-2092.
Gelman, Michael A., et al.; "Biocidal Activity of Polystyrenes That Are Cationic by Virtue of Protonation," *Organic Letters*, 2004, 4, pp. 560-557.
Gollwitzer, Hans, et al.; "Antibacterial poly(D,L-lactic acid) coating of medical implants using a biodegradable drug delivery technology", *J. Antimicrob. Chemother.*, 2003, 51, pp. 585-591.
Hanna, Hend A.; "Antibiotic-Impregnated Catheters Associated With Significant Decrease in Nosocomial and Multidrug-Resistant-Resistant Bacteremias in Critically Ill Patients", *Chest*, 2003, 124, pp. 1030-1039.
Hilal, Nidal, et al.; Photochemical modification of membrane surfaces for (bio)fouling reduction: a non-scale study using AFM, *Desalination*, 2003, 158, pp. 65-72.
Howard, G. J., et al.; "Graft Polymerisation of Methacrylic Acid on Nylon 6 Film", *J. Soc. Dyers Colour*. 1969, 85, pp. 468-473.
Hume, E.B.H., et al., "The control of *Staphylococcus epidermidis* biofilm formation and in vivo infection rates by covalently bound furanones," *Biomaterials*, 2004, 25, pp. 5023-5030.
Irikura, Hagane, et al., "Preparation of Antibacterial Polyimide Film by Vapor Deposition Polymerization," *J. Photopolym Sci. Technol.*, 2003, 16, pp. 273-276.
Jiang, Hongquan, et al., "Plasma-Enhanced Deposition of Silver Nanoparticles onto Polymer and Metal Surfaces for the Generation of Antimicrobial Characteristics," *Journal of Applied Polymer Science*, 2004, 93, pp. 1411-1422.
Kalyon, Bilge, et al.; "Antibacterial efficacy of triclosan-incorporated polyerms," *Am. J. Infect. Control*, 2001, 29, p. 124-125.
Klueh, U., et al., "Efficacy of Silver-Coated Fabric to Prevent Bacterial Colonization and Subsquent Device-Based Biofilm Formation," *J. Biomed. Mater. Res.*, 2000, 53, pp. 621-631.
Lau, Kenneth K. S., et al.; "Pulsed plasma enhanced and hot filament chemical vapor deposition of fluorocarbon films," *J. Fluor. Chem.* 2000, 104, pp. 119-126.

(Continued)

*Primary Examiner*—Lynda Salvatore
(74) *Attorney, Agent, or Firm*—Dana M. Gordon; Foley Hoag LLP

(57) ABSTRACT

One aspect of the present invention is directed to antimicrobial surfaces comprised of hydrocarbon polymers with significant hydrophobic character which also contain an amino group with a pKa greater than or equal to about 8. In certain embodiments initiated chemical vapor deposition (iCVD) is used to coat a surface with an antimicrobial polymer.

11 Claims, 12 Drawing Sheets

OTHER PUBLICATIONS

Lee, Sang Beom, et al.; "Permanent, Nonleaching Antibacterial Surfaces. 1. Synthesis by Atom Transfer Radical Polymerization," *Biomacromolecules*, 2004, 5, pp. 877-882.

Levy, Stuart B., et al.; "Antibacterial resistance worldwide: causes, challenges and responses", *Nat. Med.*, 2004, 10, pp. S122-S129.

Pryce Lewis, H.G., et al.; "Hot-Filament Chemical Vapor Deposition of Organosilicon Thin Films from Hexamethylcyclotrisiloxane and Octamethylcyclotetrasiloxane," *J. Electrochem. Soc.* 2001, 148, pp. F212-F220.

Pryce Lewis, H.G., et al.; "Perfluorooctane Sulfonyl Fluoride as an Initiator in Hot-Filament Chemical Vapor Deposition of Fluorocarbon Thin Films," *Langmuir* 2001, 17, pp. 7652-7655.

Lin, Jian, et al.; "Bactericidal Properties of Flat Surfaces and Nonoparticles Derivatized with Alkylated Polyethylenimines," *Biotechnology Progress*, 2002, 18, pp. 1082-1086.

Lin, Jian, et al.; "Insights into bactericidal action of surface-attached poly(vinyl-N-hexylpyridinium) chains", *Biotechnology Letters*, 2002, 24, pp. 801-805.

Lin, Jian, et al.; "Making thin polymeric materials, including fabrics, microbicidal and also water-repellent," *Biotechnology Letters*, 2003, 25, pp. 1661-1665.

Lin, Jian, et al.; "Mechanism of Bactericidal and Fungicidal Activities of Textiles Covalently Modified With Alkylated Polyethylenimine", *Biotechnology and Bioengineering*, 2002, 83, pp. 168-172.

Loo, Leslie. S., et al.; "Hot Filament Chemical Vapor Deposition of Polyoxymethylene as a Sacrificial Layer for Fabricating Air Gaps," *Electrochem. Solid State Lett.* 2001, 4, G81-G84.

MacKinnon, M. M., et al.; "Long-term MRSA carriage in hospital patients," *J. Hosp. Infect.*, 2000, 46, p. 216.

Mahmoud, Yehia A.-G., et al.; "Anti-Candida and mode of action of two newly synthesized polymers: a modified poly (methylmethacrylate-co-vinylbenzoylchloride) and a modified linear poly (chloroethylvinylether-co-vinylbenzoylchloride) with special reference to *Candida albicans* and *Candida tropicalis*, " *Mycopathologia*, 2004, 157, pp. 145-153.

Maki, Dennis G., et al.; "Prevention of Central Venous Catheter-Related Bloodstream Infection by Use of an Antiseptic-Impregnated Catheter," *Ann. Intern. Med.*, 1997, 127, pp. 257-266.

Mao, Yu, et al.; "Hot Filament Chemical Vapor Deposition of Poly(glycidyl methacrylate) Thin Films Using *tert*-Butyl Perioxide as an Initiator", *Langmuir* 2004, 20, pp. 2484-2488.

Munson, Erik L., et al.; "In Vitro Exposure of Bacteria to Antimicrobial Impregnated-Central Venous Catheters Does Not directly Lead to the Emergence of Antimicrobial Resistance," *Chest*, 2004, 126, pp. 1628-1636.

Murthy, Shashi K., et al.; "Initiation of Cyclic Vinylmethylsiloxane Polymerization in a Hot-Filament Chemical Vapor Deposition Process," *Langmuir* 2002, 18, pp. 6424-6248.

Neely, Alice N., et al.; "Survival of *Enterococci* and *Staphylococci* on Hospital Fabrics and Plastic," *J. Clin. Microbiol.*, 2000, 38, pp. 724-726.

Pacheco-Fowler, V. et al.; "Antiseptic impregnated endotracheal tubes for the prevention of bacterial colonization," *J. Hosp. Infect.*, 2004, 57, p. 170.

Park, Eun-Soo, et al.; Synthesis and Properties of Polymeric Biocides Based on Poly(Ethylene-*co*-Vinyl Alcohol), *Journal of Applied Polymer Science*, 2004, 93, pp. 765-770.

Raad, Issam, et al.; "Central Venous Catheters Coated with Minocycline and Rifampin for the Prevention of Catheter-Related Colonization and Bloodstream Infections," *Ann. Intern. Med.*, 1997, 127, pp. 267-274.

Rubinson, Lewis, et al.; "Best practices for insertion of central venous catheters in intensive-care units to prevent catheter-related bloodstream infections," *J. Lab. Clin. Med.*, 2004, 143, pp. 5-13.

Rupp, Mark E., et al.; "Effect of silver-coated urinary catheters: Efficacy, cost-effectiveness, and antimicrobial resistance," *Am. J. Infect. Control*, 2004, 32, pp. 445-450.

Schreuder-Gibson, Heidi L., et al.; "Chemical and Biological Protection and Detection in Fabrics for Protective Clothing," *MRS Bulletin*, 2003, 28, pp. 574-578.

Scudeller, Luigia, et al.; "MRSA carriage: the relationship between community and healthcare setting. A studyin an Italian hospital," *J. Hosp. Infect.*, 2000, 46, pp. 222-229.

Seiber, R.P., et al.; "Photo-Initiated Vapor-Phase Grafting of Acrylic Monomers onto Fibrous Substrates in the Presence of Biacetyl," *J. Appl. Polym. Sci.* 1975, 19, pp. 2187-2206.

Stephens, R., et al.; "Two episodes of life-threatening anaphylaxis in the same patient to a chlorhexidine-sulphadiazine-coated central venous catheter," *Br. J. Anaesth.*, 2001, 87, pp. 306-308.

Sun, Gang, et al.; "Chemistry of Durable and Regenerable Biocidal Textiles," *J. Chem. Educ.*, 2005, 82, pp. 60-64.

Sun, Yuyu, et al.; "Durable and Regenerable Antimicrobial Textile Materials Prepared by a Continuous Grafting Process," *Journal of Applied Polymer Science*, 2002, 84, pp. 1592-1599.

Sun, Yuyu, et al.; "Synthesis, Characterization, and Antibacterial Activities of Novel N-Halamine Polymer Beads Prepared by Suspension Copolymerization," *Macromolecules*, 2002, 35, pp. 8909-8912.

Sun, Yuyu, et al.; "Novel Refreshable N-Halamine Polymeric Biocides: Grafting Hydantoin-Containing Monomers onto High Performance Fibers by a Continuous Process," *J. Applied Polymer Sci.* 2003, 88, 1032-1039.

Tashiro, Tatsuo; "Antibacterial and Bacterium Adsorbing Macromolecules," *Macromolecular Materials and Engineering*, 2001, 286, pp. 63-87.

Thomas, Johnson, et al.; "Silicones Containing Pendant Biocides for Antifouling Coatings," *Biofouling*, 2004, 20, pp. 227-236.

Tiller, Joerg C., et al.; "Designing surfaces that kill bacteria on contact," *Proceedings of the National Academy of Sciences*, 2001, vol. 98, No. 11, pp. 5981-5985.

Tiller, Joerg C., et al.; "Polymer Surfaces Derivatized with Poly(Vinyl-N-Hexylpyridinium) Kill Airborne and Waterborne Bacteria," *Biotechnology and Bioengineering*, 2002, 79, pp. 465-471.

Tozzi, Piergiorgio, et al.; "Silver-coated prosthetic heart valve: a double-bladed weapon," *Eur. J. Cardio-Thorac. Surg.*, 2001, 19, pp. 729-731.

Tzoris, Achilles, et al.; "Testing the Durability of Polymyxin B Immobilization on a Polymer Showing Antimicrobial Activity: A Novel Approach with the Ion-Step Method," *Analytical Letters*, 2003, 36, pp. 1781-1803.

Vaara, Martti; "Agents That Increase the Permeability of the Outer Membrane," *Microbiol Rev.* 1992, 56, pp. 395-411.

Viala, J., et al.; "Agranulocytose apres application de sulfadiazine argentique chez un nourrisson de 2 mois," *Arch. Pediatr.*, 1997, 4, pp. 1103-1106.

Yue, Isaac C., et al.; "A novel polymeric chlorhexidine delivery device for the treatment of periodontal disease," *Biomaterials*, 2004, 25, pp. 3743-3750.

Yuranova, T., et al.; "Antibacterial textiles prepared by RF-plasma and vacuum-UV mediated deposition of silver," *J. Photochem. Photobiol. A-Chem.*, 2003, 161, pp. 27-34.

Gelman, M. A. et al., "Biocidal Activity of Polystyrenes That Are Cationic by Virtue of Protonation", *Organic Letters*, 6(4):557-560 (Jan. 27, 2004).

Tyler, M. P. et al., "Combinatorial initiated chemical vapor deposition for polymer thin film discovery", AICHE Annual Meeting and Fall Showcase, Conference Proceedings, *Database Compendex*,, Accession No. E2006159813147 (abstract), Engineering Information, Inc., NY, NY (2005).

Yasutake, M. et al., "Physically Controlled Radical Polymerization of Vaporized Vinyl Monomers on Surfaces. Synthesis of Block Copolymers of Methyl Methacrylate and Styrene with a Conventional Free Radical Initiator", *Macromolecules*, 36:5974-5981 (Jul. 17, 2003).

International Search Report dated Nov. 15, 2006.

* cited by examiner

[A]

[B]

CHEMICAL VAPOR DEPOSITION OF ANTIMICROBIAL POLYMER COATINGS

GOVERNMENT SUPPORT

This invention was made with support provided by the Army Research Office (Grant No. DAAD-19-02-D-0002); therefore, the government has certain rights in the invention.

BACKGROUND OF THE INVENTION

There is large and growing interest in making antimicrobial a wide variety of materials and surfaces. Textiles and other materials present in a hospital setting have been shown to be sufficient bacterial supports, raising the possibility that these materials could be responsible for disease transfer among hospital populations. A. N. Neely and M. P. Maley, *J. Clin. Microbiol.*, 2000, 38 724; M. M. MacKinnon and K. D. Allen, *J. Hosp. Infect.*, 2000, 46 216; and L. Scudeller, O. Leoncini, S. Boni, A. Navarra, A. Rezzani, S. Verdirosi, and R. Maserati, *J. Hosp. Infect.*, 2000, 46 222. Thus, it may be possible to reduce infection rates by adding antimicrobial agents to textiles and other surfaces. There has been and continues to be a considerable amount of research into making fabrics antimicrobial to address this and other issues. U. Klueh, V. Wagner, S. Kelly, A. Johnson, and J. D. Bryers, *J. Biomed. Mater. Res.*, 2000, 53 621; Y. Sun and G. Sun, *Journal of Applied Polymer Science*, 2003, 88 1032; S. Borman, *Chemical and Engineering News*, 2002, 80 36; J. Lin, S. Qiu, K. Lewis, and A. M. Klibanov, *Biotechnology and Bioengineering*, 2002, 83 168; S. M. A. El Ola, R. Kotek, W. C. White, J. A. Reeve, P. Hauser, and J. H. Kim, *Polymer*, 2004, 45 3215; T. Abel, J. I. Cohen, R. Engel, M. Filshtinskaya, A. Melkonian, and K. Melkonian, *Carbohydrate Research*, 2002, 337 2495; G. Sun and S. D. Worley, *J. Chem. Educ.*, 2005, 82 60; T. Yuranova, A. G. Rincon, A. Bozzi, S. Parra, C. Pulgarin, P. Albers, and J. Kiwi, *J. Photochem. Photobiol. A-Chem.*, 2003, 161 27; T. Tashiro, *Macromolecular Materials and Engineering*, 2001, 286 63; and H. L. Schreuder-Gibson, Q. Truong, J. E. Walker, J. R. Owens, J. D. Wander, and W. E. Jones, *MRS Bulletin*, 2003, 28 574. For instance, self-sterilizing fabrics are under study for biowarfare protection. In addition to fabrics, antimicrobial surfaces are of interest for medical devices to combat the insidious problem of biofilm formation, and for reduction of biofouling in water handling systems. I. Raad, et al., *Ann. Intern. Med.*, 1997, 127 267; D. G. Maki, S. M. Stolz, S. Wheeler, and L. A. Mermel, *Ann. Intern. Med.*, 1997, 127 257; H. Gollwitzer, K. Ibrahim, H. Meyer, W. Mittelmeier, R. Busch, and A. Stemberger, *J. Antimicrob. Chemother.*, 2003, 51 585; E. L. Munson, S. O. Heard, and G. V. Doem, *Chest*, 2004, 126 1628; M. E. Rupp, T. Fitzgerald, N. Marion, V. Helget, S. Puumala, J. R. Anderson, and P. D. Fey, *Am. J. Infect. Control*, 2004, 32 445; I. C. Yue, J. Poff, M. E. Cortes, R. D. Sinisterra, C. B. Faris, P. Hildgen, R. Langer, and V. P. Shastri, *Biomaterials*, 2004, 25 3743; V. Pacheco-Fowler, T. Gaonkar, P. C. Wyer, and S. Modak, *J. Hosp. Infect.*, 2004, 57 170; L. Rubinson and G. B. Diette, *J. Lab. Clin. Med.*, 2004, 143 5; E. B. H. Hume, et al., *Biomaterials*, 2004, 25 5023; J. K. Baveja, G. Li, R. E. Nordon, E. B. H. Hume, N. Kumar, M. D. P. Willcox, and L. A. Poole-Warren, *Biomaterials*, 2004, 25 5013; R. M. Donlan and J. W. Costerton, *Clinical Microbiology Reviews*, 2002, 15 167; J. Thomas, S. B. Choi, R. Fjeldheim, and P. Boudjouk, *Biofouling*, 2004, 20 227; and N. Hilal, L. Al-Khatib, B. P. Atkin, V. Kochkodan, and N. Potapchenko, *Desalination*, 2003, 158 65.

A wide range of antimicrobial agents have been applied to surfaces: antibiotics including chlorhexidine, rifampin and monocycline and others, silver/silver ions/silver compounds, hydantoin (also known as halamine) compounds, furanone compounds, and quaternary ammonium or phosphonium polymers. There have been a smaller number of non-permanently cationic antimicrobial polymeric materials prepared for use on surfaces, generally incorporating benzoic acid derivatives. In addition to the references cited above, see A. Tzoris, E. A. H. Hall, G. A. J. Besselink, and P. Bergveld, *Analytical Letters*, 2003, 36 1781; B. D. Kalyon and U. Olgun, *Am. J. Infect. Control*, 2001, 29 124; H. Q. Jiang, S. Manolache, A. C. L. Wong, and F. S. Denes, *Journal of Applied Polymer Science*, 2004, 93 1411; Y. Chen, S. D. Worley, T. S. Huang, J. Weese, J. Kim, C. I. Wei, and J. F. Williams, *Journal of Applied Polymer Science*, 2004, 92 363; Y. Sun and G. Sun, *Macromolecules*, 2002, 35 8909; K. Anguige, J. R. King, J. P. Ward, and P. Williams, *Math. Biosci.*, 2004, 192 39; J. Lin, J. C. Tiller, S. B. Lee, K. Lewis, and A. M. Klibanov, *Biotechnology Letters*, 2002, 24 801; J. Lin, S. Qiu, K. Lewis, and A. M. Klibanov, *Biotechnology Progress*, 2002, 18 1082; J. Lin, S. K. Murthy, B. D. Olsen, K. K. Gleason, and A. M. Klibanov, *Biotechnology Letters*, 2003, 25 1661; J. C. Tiller, S. B. Lee, K. Lewis, and A. M. Klibanov, *Biotechnology and Bioengineering*, 2002, 79 465; J. C. Tiller, C.-J. Liao, K. Lewis, and A. M. Klibanov, *Proceeding of the National Academy of Sciences*, 2001, 98 5981; S. B. Lee, R. R. Koepsel, S. W. Morley, K. Matyjaszewski, Y. J. Sun, and A. J. Russell, *Biomacromolecules*, 2004, 5 877; Y. A. G. Mahmoud and M. M. Aly, *Mycopathologia*, 2004, 157 145; H. Irikura, Y. Hasegawa, and Y. Takahashi, *J. Photopolym Sci. Technol.*, 2003, 16 273; E. S. Park, H. K. Kim, J. H. Shim, M. N. Kim, and J. S. Yoon, *Journal of Applied Polymer Science*, 2004, 93 765; and R. Chuanchuen, K. Beinlich, T. T. Hoang, A. Becher, R. R. Karkhoff-Schweizer, and H. P. Schweizer, *Antimicrob. Agents Chemother.*, 2001, 45 428.

The various agents are most often physically applied to the surface, physically impregnated into the bulk of the material, or physically incorporated into a coating that is then applied to the surface for "controlled release". In all these approaches the antimicrobial agent leaches from the surface, leading to two key problems: a limited time of effectiveness; and environmental, health and safety concerns, such as the promotion of drug resistant microbes. Non-leaching antimicrobial surfaces have been created by covalently grafting an antimicrobial polymer to the surface, atom transfer radical polymerization of an antimicrobial polymer directly from an initiating surface, and covalent attachment of an agent to a polymer chain. In the later case, any attachment scheme must not obscure the active moiety of the molecule. Also, particular care must be taken to ensure that the agent is actually covalently bound and is not just physically incorporated and that it is not releasing from the surface, which leads to the same issues discussed above for leaching antimicrobial agents.

Antibiotics have generally been employed for medical applications. Central venous catheters have been both impregnated with chlorhexidine and a silver compound and coated with rifampin/minocycline on the exterior and intraluminal surfaces to reduce successfully the rate of catheter-related blood stream infections. Each case uses two active agents in an attempt to reduce the promotion of resistant bacteria. These approaches have been successfully commercialized and are now recommended for use in certain situations, and have lead to significant reductions in mortality and healthcare costs in some hospitals. H. A. Hanna, Raad, II, B. Hackett, S. K. Wallace, K. J. Price, D. E. Coyle, and C. L. Parmley, *Chest*, 2003, 124 1030. Aside from increased cost, other factors have slowed widespread adoption of commercially available catheters that have been impregnated or coated with antibiotics. These include concerns about the emergence of drug resistant bacteria, (although this is still under study for the specific case of impregnated catheters) and cases of anaphylactic shock reaction to chlorhexidine impregnated catheters have been reported. S. B. Levy and B. Marshall, *Nat. Med.,* 2004, 10 S122; and R. Stephens, M. Mythen, P. Kallis, D. W. L. Davies, W. Egner, and A. Rickards, *Br. J. Anaesth.,* 2001, 87 306. Some in the medical profession are uneasy about employing a leaching strategy in medical devices wherein active agents are released into a compromised patient. In such cases, native and beneficial bacteria populations (e.g., *E. coli* in the intestines) may be reduced, allowing pathogenic species to gain a foothold in the patient, among other side effects. In addition to central venous catheters, the use of antibiotics has also been explored in various devices, such as a coating on wires and pins, impregnated in endotracheal tubes, and slow release from periodontal implants. In addition to medical devices, antibiotics have been covalently bound to a polymer backbone for use in a biosensor and water systems. In theory, covalently bound antibiotics would never be released, and so should not promote resistant bacteria. However, it is not yet clear what effect, if any, covalently bound antibiotics may have on the promotion of drug resistant bacteria.

Silver, silver ions, and silver compounds have been used for a somewhat more varied range of applications. Medical devices impregnated with both an antibiotic and a silver compound were discussed above. In addition, urinary catheters with a silver alloy/hydrogel coating have also been examined. Various vapor deposition methods have been employed to coat fabric and polymer/metal surfaces. No matter how the silver component is incorporated it can only work as a leaching agent because it only kills the cells after being taken up by the bacterium. Hence, any system utilizing silver will have diminishing effectiveness over time. The length of effectiveness can be increased by incorporating more silver, but at some point this becomes untenable. In addition, patient sensitivity to silver compounds and coatings has been reported. C. K. Chan, F. Jarrett, and J. A. Moylan, *J. Trauma-Injury Infect. Crit. Care,* 1976, 16 395; J. Viala, L. Simon, C. Le Pommelet, L. Philippon, D. Devictor, and G. Huault, *Arch. Pediatr.,* 1997, 4 1103; and P. Tozzi, A. Al-Darweesh, P. Vogt, and F. Stumpe, *Eur. J Cardio-Thorac. Surg.,* 2001, 19 729. In one case the patient showed no allergic reaction to topical (skin) application of silver ions yet had a strong adverse reaction to internal use of a device coated with silver. As previously discussed, the polymers system here are non-leaching and so will not lose effectiveness over time. Patient sensitivity to the new polymers has not yet been studied, but presumably a polymer system can be found that has minimal sensitivity/allergy issues.

Various hydantoin, also known as halamine, compounds have been successfully incorporated as polymer pendant groups or grafted to fabrics to impart antimicrobial action. Sun et al. have created a variety of hydantoin moieties and both incorporated them into polymer beads for water purification applications and grafted them onto various textiles to provide enhanced protection against bacteria. Worley et al. also created polymer beads with hydantoin pendant groups for water purification for comparison to polymer beads with quaternary ammonium pendant groups and found the hydantoin beads to be more effective. The hydantoin moieties are essentially storage compounds for chlorine, which is released to the impinging bacterium to kill it. Therefore, while not technically a leaching material, eventually the material is exhausted of antimicrobial protection and must be "recharged." Often, this can be done by rinsing the fabric in a sodium hypochlorite solution. However, this makes the material undesirable for cases where long term protection is desired and recharging is not realistic. In addition, the amine-halogen bond is photosensitive, somewhat limiting the use of these materials.

Furanones have been incorporated into a polymer matrix and covalently bound to the surface of catheters. Furanone compounds stop the growth of biofilms, a major route to bacterial toxicity attributed to biomaterials, by interrupting cell-to-cell communication. They do not kill individual bacterium; instead the agent simply stops them from communicating as a population to form a biofilm on a surface, and so no attachment to the surface takes place. Because of this mode of action, the authors propose that furanones are unlikely to induce bacterial resistance. However, bacteria have been able to develop resistance to a wide variety of antibiotics that act on one particular metabolic pathway. While it has not yet been shown that bacteria can develop resistance to furanones, it is easy to propose a theoretical mechanism wherein bacteria evolve to overcome the action of these agents. In addition, it is unclear that simply stopping the formation of a biofilm on a device but allowing bacteria to live will reduce infection rates. Indeed, despite reduced bacterial adhesion to the coated catheters, only a slightly reduced level of infection at the implant site in an animal model trial is reported.

Numerous quaternary ammonium, and to a lesser extent phosphonium, compounds and polymers have been shown to be effective antimicrobial agents. This work will mainly be concerned with quaternary ammonium polymers used on solid surfaces. Klibanov et al. covalently bound quaternary amine polymers, for instance poly(4-vinyl-N-alkylpyridinium bromide) and alkylated poly(ethyleneimine), to non-porous substrates and textiles by various methods for a range of potential applications. Polyquaternary amines have also been grafted to water filtration membranes for use in biofouling applications grown by atom transfer radical polymerization from a fabric surface and condensation of siloxyl compounds with an attached quaternary amine moiety. Several other quaternary ammonium and phosphonium polymers are described in a recent review. All these polymers are permanently cationic. It is thought the mechanism of action is association with the slightly negatively charged cell membrane followed by penetration and disruption of the membrane releasing the cell contents. They were shown effective against both Gram positive and Gram negative bacteria, including bacteria resistant to cationic small molecule drugs such as MRSA, and fungi. The covalent attachment schemes varied, but all involved immersing the substrate in various solvents for long periods of time and/or elevated temperatures. Often, the grafting surface required a specific functional group to covalently bond the polymer. A minimum of two steps were required in each case, grafting the polymer to the surface followed by quaternization of the amino functional group. It is possible to polymerize the quaternized monomer in some cases. The polymer coating described herein is applied to any substrate by initiated chemical vapor deposition. This process is completely solventless and the substrate is maintained at near-room temperature; thus substrates that are solvent and/or heat sensitive can be easily coated. Also, the polymer is not quaternized to a permanently cationic state, reducing the number of processing steps and processing time and avoiding a second step requiring the use of harsh solvents. The polymer can be covalently bonded to a very wide range of substrates using a grafting procedure described in more detail below. The grafting procedure is also an all-vapor phase process, with no solvents and/or elevated temperatures required.

A few antimicrobial polymers that do not contain quaternary amine or phosphine moieties have been synthesized. These have incorporated pendant groups of benzoic acid derivatives attached to a polymer backbone or benzoic acid in the backbone of a polyimide coating. In the former case the goal was to make a bulk antimicrobial polymer for use in biomedical applications instead of a surface coating. The later case has the most relevance to this work as the polyimide coating was formed by a solventless vapor deposition process, as were the polymers described herein. However, the process developed by Irikura et al. requires that the substrate withstand high temperatures, about 200° C., and thus can essentially only be used on metal substrates.

In addition, Gellman et al. developed an antimicrobial polymer that is not permanently cationic. M. Gelman, B. Weisblum, D. Lynn, and S. Gellman, *Organic Letters,* 2004, 4 557. Instead, the amino moiety has a pKa of about 10, and so the nitrogen atom is protonated to a significant extent at physiological conditions, resulting in a cationic polymer. The polymer, poly(dimethylaminomethylstyrene) was designed to adopt a similar conformation in solution as that of antimicrobial peptides. Gellman et al. compared their polymer to the similar polymer in which the amino group was quaternized and they found the non-quaternized polymer was more effective. However, the antimicrobial testing was carried out in solution and it was not apparent the same would hold true for the polymer applied to a surface, particularly because presumably the polymer would not be free to adopt the favorable conformation.

SUMMARY OF THE INVENTION

One aspect of the present invention is directed to antimicrobial surfaces comprised of hydrocarbon polymers with significant hydrophobic character which also contain an amino group with a pKa greater than or equal to about 8. In certain embodiments initiated chemical vapor deposition (iCVD) is used to coat a surface with an antimicrobial polymer. The remarkable antimicrobial polymer coatings under study here are non-leaching. Thus, they would not have a diminished effectiveness over time, greatly reduced incidence of systemic side effects, and, most significantly, it is currently thought that bacteria will not develop resistance to antimicrobial polymers although this needs to be shown for the new polymers under study here.

DETAILED DESCRIPTION OF THE INVENTION

Overview

Figure 1:
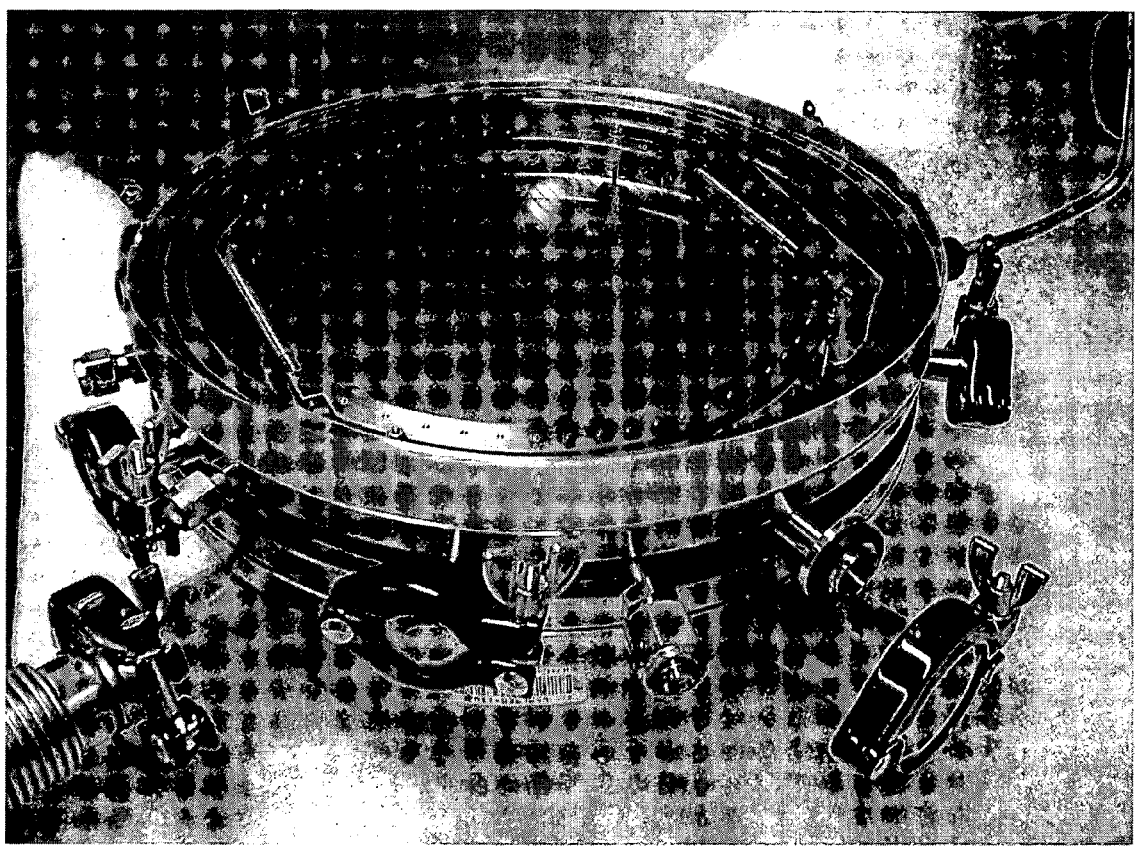
FIG. 1 depicts one embodiment of an iCVD reactor.
Figure 2:
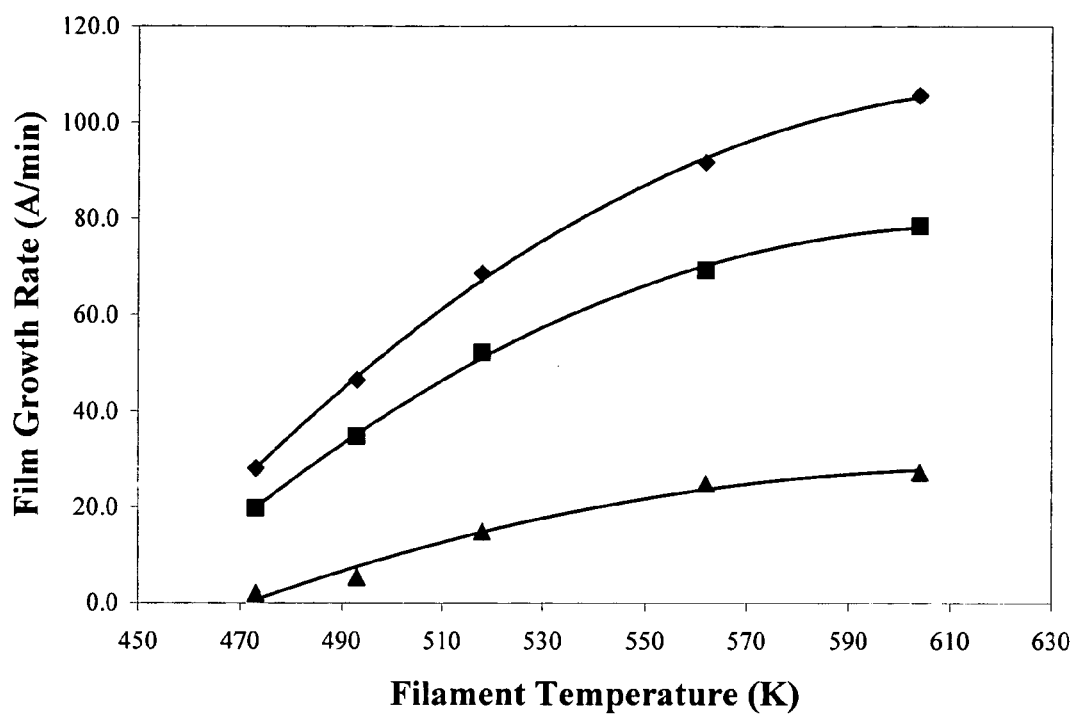
FIG. 2 depicts a growth chart for poly(dimethylaminomethylstyrene) (PDMAMS). PDMAMS with TAP, was deposited at a maximum rate of about 11 nm/min, with a $T_{filament}$ of about 260 to about 360° C., and a $T_{substrate}$ of about 47 to about 65° C. Reactor pressure was 200 mTorr and the flow rates were 2.4 sccm DMAMS and 0.6 sccm TAP.
Figure 3:
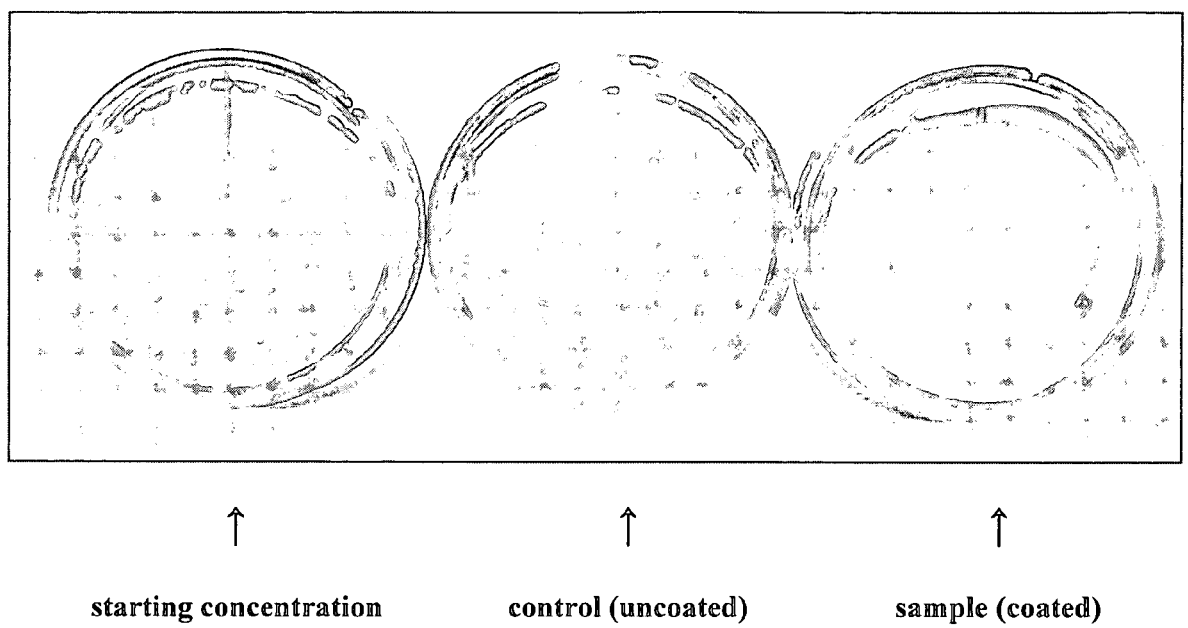
FIG. 3 depicts antimicrobial testing of fabric coated with PDMAMS. Cells were shaken with control or coated fabric (about 10 wt %) for one hour. Plates from $10^{-5}$ serial dilution cell counts are shown. The initial concentration was about $10^8$ colony forming units (CFU) per milliliter (left). The control shows no reduction (center). Coated sample has no colony forming units visible at this dilution, indicating minimum 99.9% (3 log) killing efficiency.

In general, the present invention relates to the prevention of accumulation of microorganisms on any surface, emphasizing surfaces on which such accumulation has a deleterious effect on human or animal health. The present invention relates to the prevention of those conditions effecting human or animal health that involve fouling. Fouling events involve recognition between a biologic and a surface, adhesion of the biologic to the surface, and the subsequent activity of the biologic. As understood herein, the formation of a biofilm is a type of fouling. Biofilms associated with health effects commonly contain infectious microorganisms.

In a health-related environment, fouling can result in biofilm formation. Biofilm formation is understood to cause local contamination of an affected area with potential for invasive local infection and for systemic infection. Microorganisms may damage tissues in at least three ways: 1) they can enter or contact host cells and directly cause cell death; 2) they can release endotoxins or exotoxins that kill cells at a distance, release enzymes that degrade tissue components, or damage blood vessels and cause ischemic necrosis; and 3) they can induce host-cellular responses that, although directed against the invader, may cause additional tissue damage, including suppuration, scarring and hypersensitivity reactions. An infection, whether local or systemic, represents the penetration of microorganisms into a host with the production of tissue damage or the elicitation of host defense mechanisms or both, leading to clinically identifiable symptoms. Common local symptoms can include pain, tenderness, swelling and interference with function. Common systemic symptoms can include fever, malaise and hyperdynamic cardiovascular effects. Massive bloodstream invasion by infectious agents can rapidly become fatal.

When an infection has its origins in a biofilm surrounding an object in the body, whether a naturally occurring object or a foreign one, the infection often cannot be controlled without removing that object. If the object is naturally occurring, like devascularized or necrotic tissue, it is removed surgically via a process called debridement. If the object is a foreign one, such as a medical device, it is removed entirely. At times a rim of tissue must be removed along with the contaminated object to ensure maximal removal of contaminating material. If the material being removed is essential for health, a similar article will need to be placed in the same location; however, the replacement article will be especially prone to infection because of the residual microorganisms in the area.

One aspect of the present invention is directed to antimicrobial surfaces comprising hydrocarbon polymers with significant hydrophobic character which also contain an amino group with a pKa greater than or equal to about 8. In certain embodiments, the hydrocarbon polymer is crosslinked. In certain embodiments, initiated chemical vapor deposition (iCVD) is used to coat a surface with an antimicrobial polymer. In certain embodiments, this surface acts to eliminate airborne biologics on contact, such as bacteria.

One advantage of the instant invention is that it can be practiced completely solvent-free. This advantage will become increasingly important as volatile organic compounds (VOCs) become more heavily regulated because of their environmental impact. Also, the complete lack of any solvent use is important for medical applications wherein the removal of all processing solvents from the end material is of critical importance and is often difficult to do. The substrate is held at a relatively low temperature throughout the coating process. These two facts mean that fragile substrates that are sensitive to solvents and/or heat can be coated by this process. For example, this is an advantage in coating dyed fabrics wherein the fibers are destroyed by heat and the dye is removed by organic solvents. Additionally, polymeric coatings applied from solution can contain trace amounts of solvents or plasticers left behind after processing. These trace chemicals can cause inflammatory reactions when implanted in the body. D. E. Albert, Medical Device & Diagnostic Industry, March 2002. The iCVD process offers an alternative to solvent based processes and deposits a pure polymer with negligible extractables.

In addition, the lack of a permanent cation in the antimicrobial films of the present invention is in marked contrast to the vast majority of previous work with antimicrobial polymers, which employ a quaternary amine or phosphine group. Therefore, the as-deposited polymer is an active antimicrobial with no further processing steps required, and thus greatly increases the types of substrates that can be coated. The quaternization reaction requires harsh conditions (solvent and temperature). Therefore, regardless of the coating application technique employed, the requirement for quaternization of the polymer significantly adds to the final product cost and environmental concerns.

In certain embodiments, the polymer coating process of the instant invention results in a non-leaching antimicrobial surface. This is in marked contrast to the most common current technology that involves leaching an antimicrobial drug or silver from a coating or out of the substrate itself. The leaching of drugs from a surface is of particular concern in the medical field. This can only lead to more drug-resistant microbes, already a large and growing problem in hospitals. Also, the most commonly used drugs will not kill resistant bacteria, such as methicilin-resistant *staphylococcus aureus* (MRSA) and vanomycin-resistant *enterococci* (VRE), which have already evolved and taken up residence in the majority of hospitals nationwide, and are starting to appear in the general population. Vanomycin-resistant *staphylococcus aureus* (VRSA) has also recently been isolated. Leaching antimicrobials, both drugs and silver, are depleted over time and eventually lose effectiveness, whereas the remarkable non-leaching surface coating developed here does not. Also, a small percentage of the population is sensitive to silver and has an allergic-like reaction to contact with the metal. It is thought that these same people may be sensitive to silver ions released by leaching antimicrobial coatings, leading to inflammation at the site of contact with the coating, and possibly other systemic problems.

Furthermore, a significant advantage of the coatings is that it is believed that bacteria cannot develop resistance to them. While this is difficult to prove conclusively, there have been no examples of bacteria developing resistance to this class of materials. The fact that the coating can both kill bacteria resistant to many drugs and does not cause bacteria to develop resistance makes it ideal for many applications and particularly well suited for medical applications.

As noted above, one class of antimicrobial coatings release chlorine or bromine ions to kill the bacteria. However, these coatings must be "recharged" after a time because the ions can only be released once. While recharging the coating with more chlorine only involves washing in bleach, this is not realistic, for example, for long term use in the field by military personnel. This is also detrimental for use in any medical or industrial applications. The coatings of the present invention do not release anything into the surrounding medium or bacteria, and they do not require any further treatment to stay effective over long periods of time. Hence, they are preferable from environmental, medical, and practical-usage points of view.

Definitions

For convenience, certain terms employed in the specification, examples, and appended claims are collected here.

The term "biologic" as used herein refers to any bacterium, fungus, virus, protozoan, parasite, or other infective agent capable of causing disease in humans or non-human animals.

"Contacting" as used herein refers to any means for providing the compounds of the invention to a surface to be protected from biofouling. Contacting can include spraying, wetting, immersing, dipping, painting, bonding or adhering or otherwise providing a surface with a compound of the invention.

A "component" is a part of an apparatus that is structurally integrated with that apparatus. A component may be applied to a surface of an apparatus, contained within the substance of the apparatus, retained in the interior of the apparatus, or any other arrangement whereby that part is an integral element of the structure of the apparatus. As an example, the silicone covering surrounding the mechanical part of a pacemaker is a component of the pacemaker. A component may be the lumen of an apparatus where the lumen performs some function essential to the overall function of the apparatus. The lumen of a tissue expander port is a component of the tissue expander. A component can refer to a reservoir or a discrete area within the apparatus specifically adapted for the delivery of a fluid to a surface of the apparatus. A reservoir within an implantable drug delivery device is a component of that device.

"Dressing" refer to any bandage or covering applied to a lesion or otherwise used to prevent or treat infection. Examples include wound dressings for chronic wounds (such as pressure sores, venous stasis ulcers and bums) or acute wounds and dressings over percutaneous devices such as IVs or subclavian lines intended to decrease the risk of line sepsis due to microbial invasion. For example, the compositions of the invention could be applied at the percutaneous puncture site, or could be incorporated in the adherent dressing material applied directly over the entry site.

The phrase "effective amount" refers to an amount of the disclosed antifouling compounds that significantly reduces the number of organisms that attach to a defined surface (cells/mm$^2$) relative to the number that attach to an untreated surface. Particularly preferred are amounts that reduce the number of organisms that attach to the surface by a factor of at least 2. Even more preferred are amounts that reduce the surface attachment of organisms by a factor of 4, more preferably by a factor of 6. An effective amount of the disclosed antifouling compound is said to inhibit the formation of biofilms, and to inhibit the growth of organisms on a defined surface. The term "inhibit," as applied to the effect of an antifouling compound on a surface includes any action that significantly reduces the number of organisms that attach thereto.

An "implant" is any object intended for placement in a human body that is not a living tissue. Implants include naturally derived objects that have been processed so that their living tissues have been devitalized. As an example, bone grafts can be processed so that their living cells are removed, but so that their shape is retained to serve as a template for ingrowth of bone from a host. As another example, naturally occurring coral can be processed to yield hydroxyapatite preparations that can be applied to the body for certain orthopedic and dental therapies. An implant can also be an article comprising artificial components. The term "implant" can be applied to the entire spectrum of medical devices intended for placement in a human body.

The terms "infectious microorganisms" or "infectious agents" as used herein refers to disease causing or contributing bacteria (including Gram-negative and Gram-positive organisms, such as *Staphylococci* sps. (e.g. *Staphylococcus aureus, Staphylococcus epidermis*), *Enterococcus* sp. (*E. faecalis*), *Pseudomonas* sp. (*P. aeruginosa*), *Escherichia* sp. (*E. coli*), *Proteus* sp. (*P. mirabilis*)), fungi (including *Candida albicans*), viruses and protists.

"Medical device" refers to a non-naturally occurring object that may be, is or has been inserted or implanted in a subject or applied to a surface of a subject. Medical devices can be made of a variety of biocompatible materials, including: metals, ceramics, polymers, gels and fluids not normally found within the human body. Examples of polymers useful in fabricating medical devices include such polymers as silicones, rubbers, latex, plastics, polyanhydrides, polyesters, polyorthoesters, polyamides, polyacrylonitrile, polyurethanes, polyethylene, polytetrafluoroethylene, polyethylenetetraphthalate and polyphazenes. Medical devices can also be fabricated using certain naturally-occurring materials or treated naturally-occurring materials. As an example, a heart valve can be fabricated by combining a treated porcine heart valve with an affixation apparatus using artificial materials. Medical devices can include any combination of artificial materials, combinations selected because of the particular characteristics of the components. For example, a hip implant can include a combination of a metallic shaft to bear the weight, a ceramic artificial joint and a polymeric glue to affix the structure to the surrounding bone. An implantable device is one intended to be completely imbedded in the body without any structure left outside the body (e.g. heart valve). An insertable device is one that is partially imbedded in the body but has a part intended to be external (e.g. a catheter or a drain). Medical devices can be intended for short-term or long-term residence where they are positioned. A hip implant is intended for several decades of use, for example. By contrast, a tissue expander may only be needed for a few months, and is removed thereafter. Insertable devices tend to remain in place for shorter times than implantable devices, in part because they come into more contact with microorganisms that can colonize them.

The term "soluble" refers to the ability to be loosened or dissolved.

The term "surface" or "surfaces" can mean any surface of any material, including glass, plastics, metals, polymers, and like. It can include surfaces constructed out of more than one material, including coated surfaces. Non-limiting examples of surfaces include nylon, polyester, polyurethane, polyanhydride, polyorthoester, polyacrylonitrile, polyphenazine, latex, teflon, dacron, acrylate polymer, chlorinated rubber, fluoropolymer, polyamide resin, vinyl resin, Gore-tex®, Marlex®, expanded polytetrafluoroethylene (e-PTFE), low density polyethylene (LDPE), high density polyethylene (HDPE), polypropylene (PP), and poly(ethylene terephthalate) (PET).

Biofilm formation with health implications can involve those surfaces in all health-related environments, including surfaces found in medical environments and those surfaces in industrial or residential environments that are involved in those functions essential to well-being like nutrition, sanitation and the prevention of disease.

A surface of an article adapted for use in a medical environment can be capable of sterilization using autoclaving, biocide exposure, irradiation or gassing techniques like ethylene oxide exposure. Surfaces found in medical environments include the inner and outer aspects of various instruments and devices, whether disposable or intended for repeated uses. Examples include the entire spectrum of articles adapted for medical use, including scalpels, needles, scissors and other devices used in invasive surgical, therapeutic or diagnostic procedures; implantable medical devices, including artificial blood vessels, catheters and other devices for the removal or delivery of fluids to patients, artificial hearts, artificial kidneys, orthopedic pins, plates and implants; catheters and other tubes (including urological and biliary tubes, endotracheal tubes, peripherably insertable central venous catheters, dialysis catheters, long term tunneled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, heart valves, artificial joints, artificial larynxes, otological implants), vascular catheter ports, wound drain tubes, hydrocephalus shunts, pacemakers and implantable defibrillators, and the like. Other examples will be readily apparent to practitioners in these arts.

Surfaces found in the medical environment include also the inner and outer aspects of pieces of medical equipment, medical gear worn or carried by personnel in the health care setting. Such surfaces can include counter tops and fixtures in areas used for medical procedures or for preparing medical apparatus, tubes and canisters used in respiratory treatments, including the administration of oxygen, of solubilized drugs in nebulizers and of anesthetic agents. Also included are those surfaces intended as biological barriers to infectious organisms in medical settings, such as gloves, aprons and faceshields. Commonly used materials for biological barriers may be latex-based or non-latex based. Vinyl is commonly used as a material for non-latex surgical gloves. Other such surfaces can include handles and cables for medical or dental equipment not intended to be sterile. Additionally, such surfaces can include those non-sterile external surfaces of tubes and other apparatus found in areas where blood or body fluids or other hazardous biomaterials are commonly encountered.

The term 'Gram-positive bacteria' is an art recognized term for bacteria characterized by having as part of their cell wall structure peptidoglycan as well as polysaccharides and/or teichoic acids and are characterized by their blue-violet color reaction in the Gram-staining procedure. Representative Gram-positive bacteria include: *Actinomyces* spp., *Bacillus anthracis*, *Bifidobacterium* spp., *Clostridium botulinum*, *Clostridium perfringens*, *Clostridium* spp., *Clostridium tetani*, *Corynebacterium diphtheriae*, *Corynebacterium jeikeium*, *Enterococcus faecalis*, *Enterococcus faecium*, *Erysipelothrix rhusiopathiae*, *Eubacterium* spp., *Gardnerella vaginalis*, *Gemella morbillorum*, *Leuconostoc* spp., *Mycobacterium abcessus*, *Mycobacterium avium* complex, *Mycobacterium chelonae*, *Mycobacterium fortuitum*, *Mycobacterium haemophilium*, *Mycobacterium kansasii*, *Mycobacterium leprae*, *Mycobacterium marinum*, *Mycobacterium scrofulaceum*, *Mycobacterium smegmatis*, *Mycobacterium terrae*, *Mycobacterium tuberculosis*, *Mycobacterium ulcerans*, *Nocardia* spp., *Peptococcus niger*, *Peptostreptococcus* spp., *Proprionibacterium* spp., *Staphylococcus aureus*, *Staphylococcus auricularis*, *Staphylococcus capitis*, *Staphylococcus cohnii*, *Staphylococcus epidermidis*, *Staphylococcus haemolyticus*, *Staphylococcus hominis*, *Staphylococcus lugdanensis*, *Staphylococcus saccharolyticus*, *Staphylococcus saprophyticus*, *Staphylococcus schleiferi*, *Staphylococcus similans*, *Staphylococcus warneri*, *Staphylococcus xylosus*, *Streptococcus agalactiae* (group B *streptococcus*), *Streptococcus anginosus*, *Streptococcus bovis*, *Streptococcus canis*, *Streptococcus equi*, *Streptococcus milleri*, *Streptococcus mitior*, *Streptococcus mutans*, *Streptococcus pneumoniae*, *Streptococcus pyogenes* (group A *streptococcus*), *Streptococcus salivarius*, *Streptococcus sanguis*.

The term "Gram-negative bacteria" is an art recognized term for bacteria characterized by the presence of a double membrane surrounding each bacterial cell. Representative Gram-negative bacteria include *Acinetobacter calcoaceticus*, *Actinobacillus actinomycetemcomitans*, *Aeromonas hydrophila*, *Alcaligenes xylosoxidans*, *Bacteroides*, *Bacteroides fragilis*, *Bartonella bacilliformis*, *Bordetella* spp., *Borrelia burgdorferi*, *Branhamella catarrhalis*, *Brucella* spp., *Campylobacter* spp., *Chalmydia pneumoniae*, *Chlamydia psittaci*, *Chlamydia trachomatis*, *Chromobacterium violaceum*, *Citrobacter* spp., *Eikenella corrodens*, *Enterobacter aerogenes*, *Escherichia coli*, *Flavobacterium meningosepticum*, *Fusobacterium* spp., *Haemophilus influenzae*, *Haemophilus* spp., *Helicobacter pylori*, *Klebsiella* spp., *Legionella* spp., *Leptospira* spp., *Moraxella catarrhalis*, *Morganella morganii*, *Mycoplasma pneumoniae*, *Neisseria gonorrhoeae*, *Neisseria meningitidis*, *Pasteurella multocida*, *Plesiomonas shigelloides*, *Prevotella* spp., *Proteus* spp., *Providencia rettgeri*, *Pseudomonas aeruginosa*, *Pseudomonas* spp., *Rickettsia prowazekii*, *Rickettsia rickettsii*, *Rochalimaea* spp., *Salmonella* spp., *Salmonella typhi*, *Serratia marcescens*, *Shigella* spp., *Treponema carateum*, *Treponema pallidum*, *Treponema pallidum endemicum*, *Treponema pertenue*, *Veillonella* spp., *Vibrio cholerae*, *Vibrio vulnificus*, *Yersinia enterocolitica*, *Yersinia pestis*.

The term "polar" is art-recognized. A polar compound has an asymmetric charge distribution. In general, a non-polar substance will dissolve non-polar molecules, and a polar substance will dissolve polar molecules, e.g. water, a polar substance, dissolves other polar substances. An amphipathic compound has a portion which is soluble in aqueous solvents, and a portion which is insoluble aqueous solvents.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms.

Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle" is art-recognized and refers to an aromatic or non-aromatic ring in which each atom of the ring is carbon.

The term "nitro" is art-recognized and refers to —$NO_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —$SO_2^-$. "Halide" designates the corresponding anion of the halogens, and "pseudohalide" has the definition set forth on page 560 of "Advanced Inorganic Chemistry" by Cotton and Wilkinson.

The terms "amine" and "amino" are art-recognized and refer to both unsubstituted and substituted amines, e.g., a moiety that may be represented by the general formulas:

wherein R50, R51 and R52 each independently represent a hydrogen, an alkyl, an alkenyl, —$(CH_2)_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —$(CH_2)_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

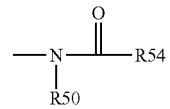

wherein R50 is as defined above, and R54 represents a hydrogen, an alkyl, an alkenyl or —$(CH_2)_m$—R61, where m and R61 are as defined above.

The term "amido" is art recognized as an amino-substituted carbonyl and includes a moiety that may be represented by the general formula:

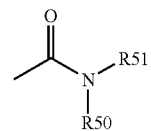

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—$(CH_2)_m$—R61, wherein m and R61 are defined above. Representative alkylthio groups include methylthio, ethyl thio, and the like.

The term "carboxyl" is art recognized and includes such moieties as may be represented by the general formulas:

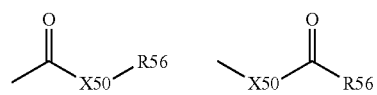

wherein X50 is a bond or represents an oxygen or a sulfur, and R55 and R56 represents a hydrogen, an alkyl, an alkenyl, —$(CH_2)_m$—R61 or a pharmaceutically acceptable salt, R56 represents a hydrogen, an alkyl, an alkenyl or —$(CH_2)_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C=O)NRR', where R and R' are independently H, aliphatic groups, aryl groups or heteroaryl groups.

The term "oxo" refers to a carbonyl oxygen (=O).

The terms "oxime" and "oxime ether" are art-recognized and refer to moieties that may be represented by the general formula:

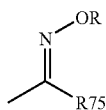

wherein R75 is hydrogen, alkyl, cycloalkyl, alkenyl, alkynyl, aryl, aralkyl, or —(CH$_2$)$_m$—R61. The moiety is an "oxime" when R is H; and it is an "oxime ether" when R is alkyl, cycloalkyl, alkenyl, alkynyl, aryl, aralkyl, or —(CH$_2$)$_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

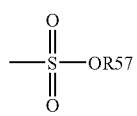

in which R57 is an electron pair, hydrogen, alkyl, cycloalkyl, or aryl.

The term "sulfate" is art recognized and includes a moiety that may be represented by the general formula:

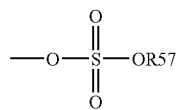

in which R57 is as defined above.

The term "sulfonamido" is art recognized and includes a moiety that may be represented by the general formula:

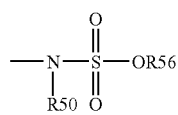

in which R50 and R56 are as defined above.

The term "sulfamoyl" is art-recognized and refers to a moiety that may be represented by the general formula:

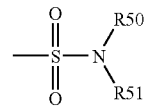

in which R50 and R51 are as defined above.

The term "sulfonyl" is art-recognized and refers to a moiety that may be represented by the general formula:

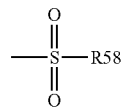

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

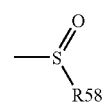

in which R58 is defined above.

The term "phosphoryl" is art-recognized and may in general be represented by the formula:

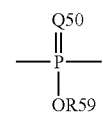

wherein Q50 represents S or O, and R59 represents hydrogen, a lower alkyl or an aryl. When used to substitute, e.g., an alkyl, the phosphoryl group of the phosphorylalkyl may be represented by the general formulas:

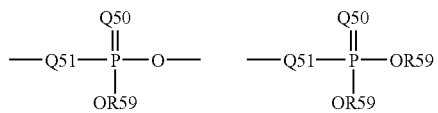

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

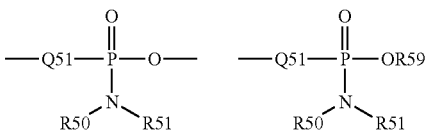

wherein Q51, R50, R51 and R59 are as defined above.

The term "phosphonamidite" is art-recognized and may be represented in the general formulas:

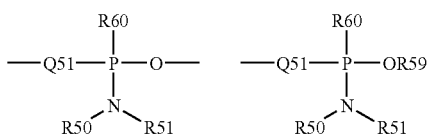

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The definition of each expression, e.g. alkyl, m, n, and the like, when it occurs more than once in any structure, is intended to be independent of its definition elsewhere in the same structure.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

As used here "-alkyl" refers to a radical such as —$CH_2CH_3$, while "-alkyl-" refers to a diradical such as —$CH_2CH_2$—.

For purposes of this invention, the chemical elements are identified in accordance with the Periodic Table of the Elements, CAS version, "Handbook of Chemistry and Physics", 67th Ed., 1986-87, inside cover.

The phrase "polydispersity index" refers to the ratio of the "weight average molecular weight" to the "number average molecular weight" for a particular polymer; it reflects the distribution of individual molecular weights in a polymer sample.

The phrase "weight average molecular weight" refers to a particular measure of the molecular weight of a polymer. The weight average molecular weight is calculated as follows: determine the molecular weight of a number of polymer molecules; add the squares of these weights; and then divide by the total weight of the molecules.

The phrase "number average molecular weight" refers to a particular measure of the molecular weight of a polymer. The number average molecular weight is the common average of the molecular weights of the individual polymer molecules. It is determined by measuring the molecular weight of n polymer molecules, summing the weights, and dividing by n.

Composition of the Polymer

The composition of the polymer of the invention can vary. In certain embodiments, the polymers of the instant invention are hydrocarbon polymers, with significant hydrophobic character, and they contain at least one amino group with a pKa of greater than or equal to about 8. This means that, at conditions below a pH of 8, a significant portion of the amino groups will be protonated and cationic. Furthermore, in certain embodiments, the degree of polymer crosslinking can be controlled by adding a difunctional monomer or by increasing the energy input to the process. Crosslinking can increase the durability and adhesion of the coating without effecting the effectiveness. Cross-linking agents include, but are not limited to, 2-ethyl-2(hydroxymethyl)propane-trimethyacrylate (TRIM), acrylic acid, methacrylic acid, trifluoro-methacrylic acid, 2-vinylpyridine, 4-vinylpyridine, 3(5)-vinylpyridine, p-methylbenzoic acid, itaconic acid, 1-vinylimidazole, and mixtures thereof.

One aspect of the present invention relates to a composition, comprising a surface and a polymer coating, wherein said polymer coating comprises a plurality of monomers represented by formula I or II or both:

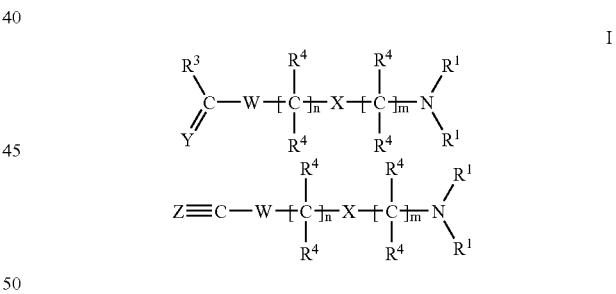

wherein, independently for each occurrence,

W is —C(=O)O—, —C(=O)N(R)—, —C(=O)S—, —C($R^4$)$_2$—, —C(=O)—, —C(=NR)—, —C(=S)—, —C($R^4$)=C($R^4$)—, —C≡C—, -cycloalkyl-, -heterocycloalkyl-, -cycloalkenyl-, -heterocycloalkenyl-, -aryl-, or -heteroaryl-;

X is absent, —O—, —N(R)—, —S—, —C(=O)O—, —C(=O)N(R)—, —C(=O)S—, —S(=O)—, —S(=O)$_2$—, —C($R^4$)$_2$—, —C(=O)—, —C(=NR)—, —C(=S)—, —C($R^4$)=C($R^4$)—, —C≡C—, -cycloalkyl-, -heterocycloalkyl-, -cycloalkenyl-, -heterocycloalkenyl-, -aryl-, or -heteroaryl-;

Y is C($R^2$)$_2$ or N($R^2$); or Z is C($R^2$) or N;

R is -hydrogen, -halogen, -alkyl, -cycloalkyl, -heterocycloalkyl, -alkenyl, -cycloalkenyl, -heterocycloalkenyl, -alkynyl, -cyano, -aryl, or -heteroaryl;

$R^1$ is -hydrogen, -halogen, -alkyl, -cycloalkyl, -heterocycloalkyl, -alkenyl, -cycloalkenyl, -heterocycloalkenyl, -alkynyl, -aryl, -heteroaryl or —[C(R)$_2$]$_p$—R;

$R^2$ is -hydrogen, -halogen, -alkyl, -cycloalkyl, -heterocycloalkyl, -alkenyl, -cycloalkenyl, -heterocycloalkenyl, -alkynyl, -aryl, -heteroaryl or —[C(R)$_2$]$_p$—R;

$R^3$ is -hydrogen, -halogen, -alkyl, -cycloalkyl, -heterocycloalkyl, -alkenyl, -cycloalkenyl, -heterocycloalkenyl, -alkynyl, -aryl, -heteroaryl or —[C(R)$_2$]$_p$—R;

$R^4$ is -hydrogen, -halogen, -alkyl, -cycloalkyl, -heterocycloalkyl, -alkenyl, -cycloalkenyl, -heterocycloalkenyl, -alkynyl, -aryl, -heteroaryl or —[C(R)$_2$]$_p$—R;

m is 0-7 inclusive;

n is 0-7 inclusive; and p is 0-10 inclusive.

In certain embodiments, the present invention relates to the aforementioned composition, wherein Y is C(R$^2$)$_2$ or Z is C(R$^2$).

In certain embodiments, the present invention relates to the aforementioned composition, wherein Y is CH$_2$ or Z is CH.

In certain embodiments, the present invention relates to the aforementioned composition, wherein R$^3$ is -hydrogen or -alkyl.

In certain embodiments, the present invention relates to the aforementioned composition, wherein R$^3$ is -hydrogen or -methyl.

In certain embodiments, the present invention relates to the aforementioned composition, wherein R$^1$ is -alkyl.

In certain embodiments, the present invention relates to the aforementioned composition, wherein R$^1$ is -methyl.

In certain embodiments, the present invention relates to the aforementioned composition, wherein X is —C(R$^4$)$_2$—. In certain embodiments, the present invention relates to the aforementioned composition, wherein R$^4$ is hydrogen.

In certain embodiments, the present invention relates to the aforementioned composition, wherein X is —C(R$^4$)$_2$—; and R$^4$ is -hydrogen.

In certain embodiments, the present invention relates to the aforementioned composition, wherein Y is CH$_2$ or Z is CH; R$^3$ is -hydrogen or -methyl; R$^1$ is -methyl; X is —C(R$^4$)$_2$—; and R$^4$ is -hydrogen.

Another aspect of the present invention relates to a composition, comprising a surface and a polymer coating, wherein said polymer coating comprises a plurality of monomers represented by formula III:

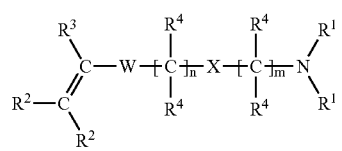

III wherein, independently for each occurrence,

W is

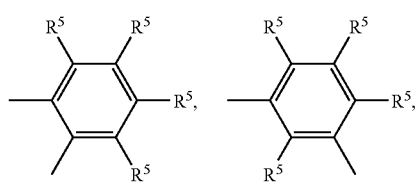

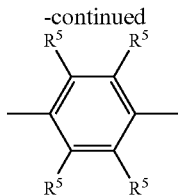

or —C(=O)O—;

X is absent, —O—, —N(R)—, —S—, —C(=O)O—, —C(=O)N(R)—, —C(=O)S—, —S(=O)—, —S(=O)$_2$—, —C(R$^4$)$_2$—, —C(=O)—, —C(=NR)—, —C(=S)—, —C(R$^4$)=C(R$^4$)—, —C≡C—, -cycloalkyl-, -heterocycloalkyl-, -cycloalkenyl-, -heterocycloalkenyl-, -aryl-, or -heteroaryl-;

R is -hydrogen, -halogen, -alkyl, -cycloalkyl, -heterocycloalkyl, -alkenyl, -cycloalkenyl, -heterocycloalkenyl, -alkynyl, -cyano, -aryl, or -heteroaryl;

$R^1$ is -hydrogen, -halogen, -alkyl, -cycloalkyl, -heterocycloalkyl, -alkenyl, -cycloalkenyl, -heterocycloalkenyl, -alkynyl, -aryl, -heteroaryl or —[C(R)$_2$]$_p$—R;

$R^2$ is -hydrogen, -halogen, -alkyl, -cycloalkyl, -heterocycloalkyl, -alkenyl, -cycloalkenyl, -heterocycloalkenyl, -alkynyl, -aryl, -heteroaryl or —[C(R)$_2$]$_p$—R;

$R^3$ is -hydrogen, -halogen, -alkyl, -cycloalkyl, -heterocycloalkyl, -alkenyl, -cycloalkenyl, -heterocycloalkenyl, -alkynyl, -aryl, -heteroaryl or —[C(R)$_2$]$_p$—R;

$R^4$ is -hydrogen, -halogen, -alkyl, -cycloalkyl, -heterocycloalkyl, -alkenyl, -cycloalkenyl, -heterocycloalkenyl, -alkynyl, -aryl, -heteroaryl or —[C(R)$_2$]$_p$—R;

$R^5$ is -hydrogen, -halogen, -alkyl, -cycloalkyl, -heterocycloalkyl, -alkenyl, -cycloalkenyl, -heterocycloalkenyl, -alkynyl, -aryl, -heteroaryl or —[C(R)$_2$]$_p$—R;

m is 0-4 inclusive;

n is 0-4 inclusive; and p is 0-10 inclusive.

In certain embodiments, the present invention relates to the aforementioned composition, wherein W is

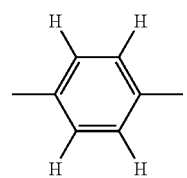

or —C(=O)O—.

In certain embodiments, the present invention relates to the aforementioned composition, wherein n is 0.

In certain embodiments, the present invention relates to the aforementioned composition, wherein n is 1.

In certain embodiments, the present invention relates to the aforementioned composition, wherein n is 2.

In certain embodiments, the present invention relates to the aforementioned composition, wherein n is 3.

In certain embodiments, the present invention relates to the aforementioned composition, wherein n is 4.

In certain embodiments, the present invention relates to the aforementioned composition, wherein m is 0.

In certain embodiments, the present invention relates to the aforementioned composition, wherein m is 1.

In certain embodiments, the present invention relates to the aforementioned composition, wherein m is 2.

In certain embodiments, the present invention relates to the aforementioned composition, wherein m is 3.

In certain embodiments, the present invention relates to the aforementioned composition, wherein m is 4.

In certain embodiments, the present invention relates to the aforementioned composition, wherein $R^1$ is -alkyl.

In certain embodiments, the present invention relates to the aforementioned composition, wherein $R^1$ is -methyl or -ethyl.

In certain embodiments, the present invention relates to the aforementioned composition, wherein $R^2$ is -hydrogen or -alkyl.

In certain embodiments, the present invention relates to the aforementioned composition, wherein $R^2$ is -hydrogen or -methyl.

In certain embodiments, the present invention relates to the aforementioned composition, wherein $R^3$ is -hydrogen.

In certain embodiments, the present invention relates to the aforementioned composition, wherein $R^4$ is -hydrogen.

In certain embodiments, the present invention relates to the aforementioned composition, wherein W is

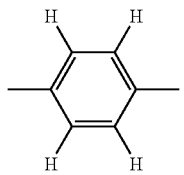

or —C(=O)O—; and $R^3$ is -hydrogen.

In certain embodiments, the present invention relates to the aforementioned composition, wherein W is

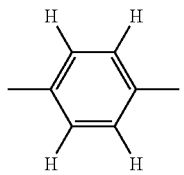

or —C(=O)O—; $R^3$ is -hydrogen; and $R^2$ is -hydrogen or methyl.

In certain embodiments, the present invention relates to the aforementioned composition, wherein W is

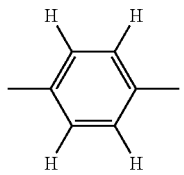

or —C(=O)O—; $R^3$ is -hydrogen; and $R^2$ is -hydrogen or methyl; and $R^1$ is alkyl.

In certain embodiments, the present invention relates to the aforementioned composition, wherein W is

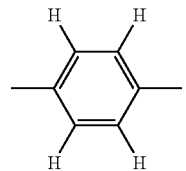

or —C(=O)O—; $R^3$ is -hydrogen; and $R^2$ is -hydrogen or methyl; $R^1$ is alkyl; X is —C($R^4$)$_2$—; and $R^4$ is -hydrogen.

In certain embodiments, the present invention relates to the aforementioned composition, wherein W is

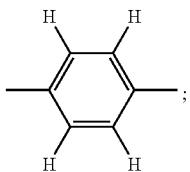

$R^3$ is -hydrogen; and $R^2$ is -hydrogen; $R^1$ is methyl; X is —C($R^4$)$_2$—; $R^4$ is -hydrogen; m is 0; and n is 0.

In certain embodiments, the present invention relates to the aforementioned composition, wherein W is —C(=O)O—; $R^3$ is -hydrogen; and $R^2$ is -methyl; $R^1$ is ethyl; X is —C($R^4$)$_2$—; $R^4$ is -hydrogen; m is 1; and n is 0.

Another aspect of the present invention relates to a composition, comprising a surface and a polymer coating, wherein said polymer coating comprises a plurality of monomers selected from the group consisting of styrenes and acrylates.

Another aspect of the present invention relates to a composition, comprising a surface and a polymer coating, wherein said polymer coating comprises a plurality of monomers selected from the group consisting of (dimethylaminomethyl)styrene, (dimethylaminoethyl)styrene, (diethylaminomethyl)styrene, (diethylaminoethyl)styrene, (dimethylaminomethyl)-α-methylstyrene, (diethylaminoethyl)acrylate, (dimethylaminoethyl)acrylate, (diethylaminomethyl)acrylate, (dimethylaminomethyl)acrylate, (dimethylaminopropyl)acrylate, (diethylaminoethyl)methacrylate, (dimethylaminoethyl)methacrylate, (diethylaminomethyl)methacrylate, (dimethylaminomethyl)methacrylate and (dimethylaminopropyl)methacrylate.

In certain embodiments, the present invention relates to the aforementioned composition, wherein said plurality of monomers is selected from the group consisting of (dimethylaminomethyl)styrene and (diethylaminoethyl)acrylate.

In certain embodiments, the present invention relates to the aforementioned composition, wherein said polymer coating has a mass per surface area of less than about 500 µg/cm$^2$.

In certain embodiments, the present invention relates to the aforementioned composition, wherein said polymer coating has a mass per surface area of less than about 100 µg/cm$^2$.

In certain embodiments, the present invention relates to the aforementioned composition, wherein said polymer coating has a mass per surface area of less than about 50 µg/cm$^2$.

In certain embodiments, the present invention relates to the aforementioned composition, wherein said polymer coating has a mass per surface area of less than about 10 µg/cm$^2$.

In certain embodiments, the present invention relates to the aforementioned composition, wherein said polymer coating has a mass per surface area of less than about 5 µg/cm$^2$.

Figure 5:
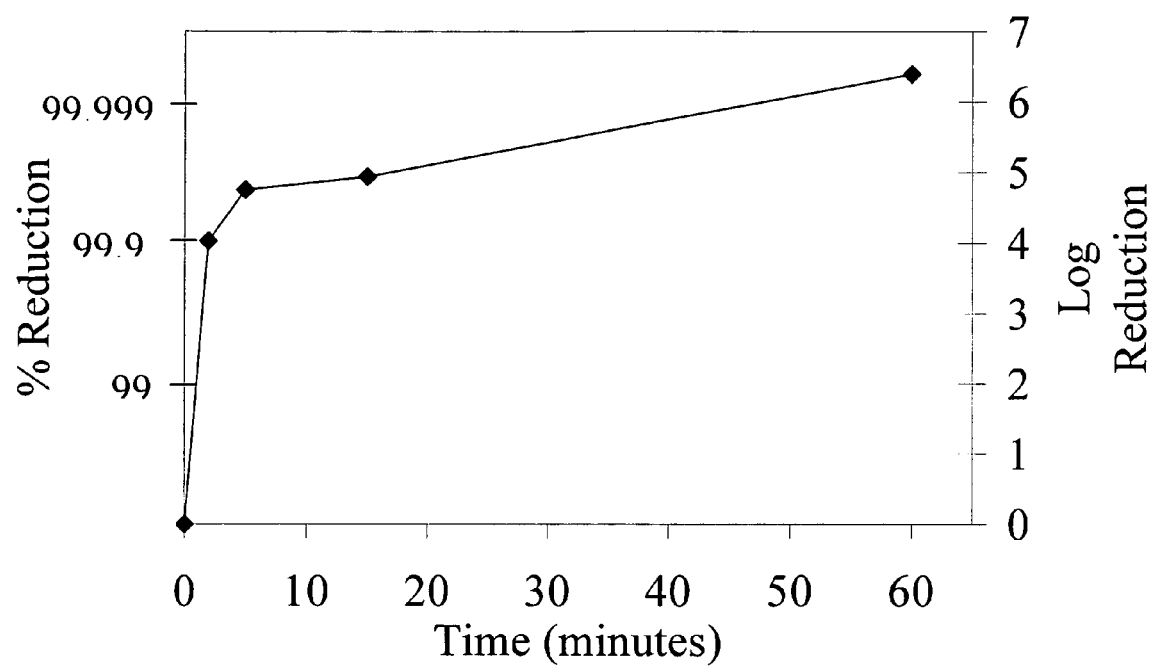
FIG. 5 depicts antimicrobial testing of PDMAMS coatings on fabric; Time series. With 39 µg polymer/cm$^2$ of fabric. A kill of 99.9999% was observed after 1 hour. Method used: ASTM E2149-01 "Determining the Antimicrobial Activity of Immobilized Antimicrobial Agents Under Dynamic Contact Conditions." The microbe used was *E. coli* (ATCC 29425).
Figure 6:
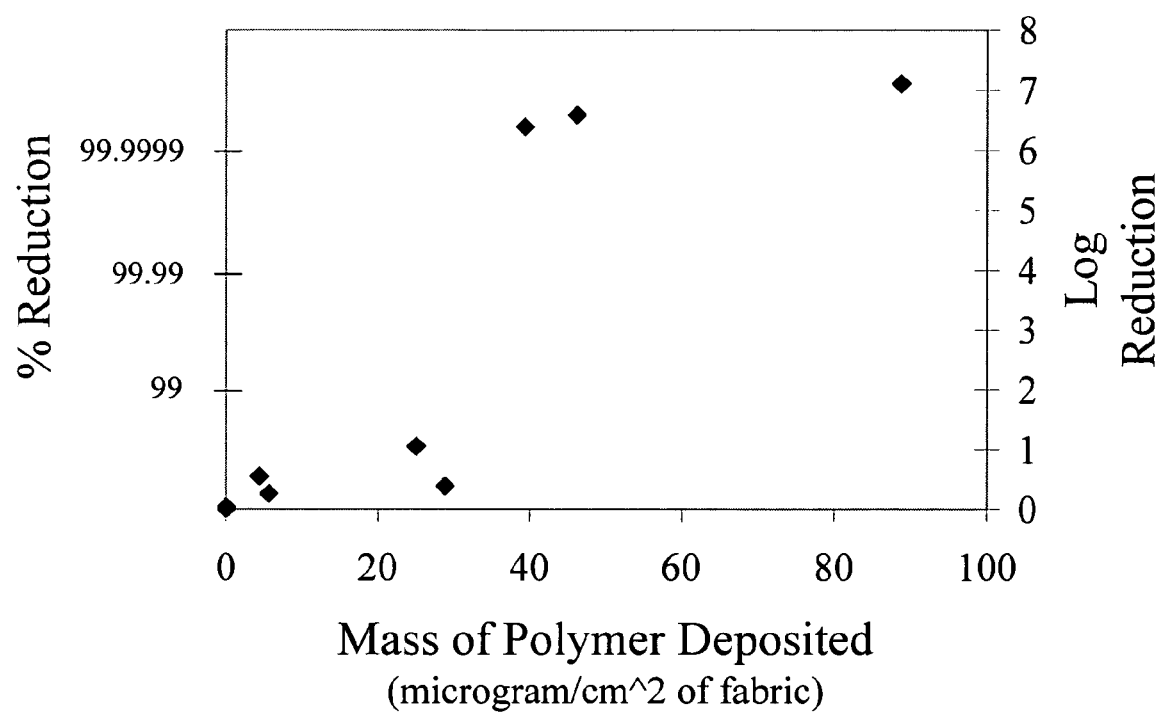
FIG. 6 depicts antimicrobial testing of PDMAMS coatings on fabric; Mass series. With 39 µg polymer/cm$^2$ of fabric a 99.9999% kill was observed. Method used: ASTM E2149-01 "Determining the Antimicrobial Activity of Immobilized Antimicrobial Agents Under Dynamic Contact Conditions." The microbe used was *E. coli* (ATCC 29425). Due to test procedures, some points indicate the maximum possible value.

The required mass per surface area depends on the specific surface area of the substrate to be coated. A smooth flat substrate, 1 cm$^2$ in area requires coverage of only 1 cm$^2$ of area and thus the specific surface area of 1 cm$^2$/cm$^2$. However, a 1 cm$^2$ section of fabric has a specific surface area greater than 1 because each surface-accessible fiber of the fabric must be coated. The gaseous reactants of the iCVD process are able to penetrate into the fabric and coat these internal surfaces. The specific surface area will depend on the packing density of the fibers and total thickness of the fabric. The thickness (cm) of the coating multiplied by the specific surface area (cm$^2$/cm$^2$) of the fabric and the density of the coating (g/cm$^3$) will yield the mass per surface area (g/cm$^2$). For the fabric shown in FIG. 12, the mass per surface area of 39 µg/cm$^2$ at which a high kill efficiency is observed (FIG. 5) corresponds to a thickness of approximately 50 nm surrounding each fiber based on estimates of the fabric's specific surface area and the density of the coatings. If the same thickness of 50 nm was applied to a flat substrate, the mass per surface area would be approximate 5 µg/cm$^2$.

In certain embodiments, the present invention relates to the aforementioned composition, wherein said polymer coating is covalently bound to the surface.

In certain embodiments, the present invention relates to the aforementioned composition, wherein said surface is selected from the group consisting of nylon, polyester, polyurethane, polyanhydride, polyorthoester, polyacrylonitrile, polyphenazine, latex, teflon, dacron, acrylate polymer, chlorinated rubber, fluoropolymer, polyamide resin, vinyl resin, Gore-tex®, Marlex®, expanded polytetrafluoroethylene (e-PTFE), low density polyethylene (LDPE), high density polyethylene (HDPE), polypropylene (PP), and poly(ethylene terephthalate) (PET).

In certain embodiments, the present invention relates to the aforementioned composition, wherein said surface is the surface of a medical device.

In certain embodiments, the present invention relates to the aforementioned composition, wherein said surface is the surface of a medical device; and said medical device is selected from the group consisting of pins, screws, plates, ventriculoatrial shunts, ventriculoperitoneal shunts, dialysis shunts, heart valves, pacemakers, infusion pumps, vascular grafting prostheses, stents, sutures, surgical meshes, replacement prostheses, breast implants, tissue expanders, contact lenses, stoma appliances, artificial larynx, endotracheal tubes, tracheal tubes, gastrostomy tubes, biliary drainage tubes, biliary stents, catheters, bandages, adhesive tapes, and clear plastic adherent sheets.

Deposition of Coatings

In addition to initiated chemical vapor deposition methodology, described below in detail, the antimicrobial polymer coatings of the invention may also be deposited using several other monomer and free radical initiating species: such as, plasma excitation without an initiator species (known generally as plasma-enhanced CVD) or photo-initiation of a UV sensitive initiator species (such as the peroxide or "azo" classes of molecules; e.g., t-butylperoxide or 2,2'-azobis(2-methylpropane)) or the monomer alone if the monomer is UV sensitive. Also, a method for enhancing coating bonding to the substrate, known generally as "grafting," may be used to affix the antimicrobial polymers to a surface.

In one embodiment of the invention, an antimicrobial polymer coating is applied via initiated chemical vapor deposition (iCVD). Initiated chemical vapor deposition is capable of producing a range of polymeric and multifunctional nano-coatings. Coatings can be made extremely thin (down to about 10 nm) on objects with dimensions in the nanometer range (e.g., carbon nanotubes). Importantly, the object to be coated remains at room temperature, which means that nanothin coatings can be prepared on materials ranging from plastics to metals. The process is also conformal, which means it provides uniform coverage on objects which have small, complex, three-dimensional geometries.

Initiated CVD generally takes place in a reactor. Precursor molecules, consisting of initiator and monomer species, are fed into the reactor. This can take place at a range of pressures from atmospheric pressure to low vacuum. An extremely thin, conformal layer of monomer molecules continually adsorbs to the substrate surface. The initiator is broken down through the addition of thermal energy or radiative energy (UV) to form free radicals, which subsequently add to a monomer molecule and cause polymerization to proceed in a manner analogous to well-known solution polymerization. In this manner, complex substrates can be conformably coated. During the deposition the substrate is kept at a relatively low temperature, generally room temperature up to about 60° C. The process is solvent-free. The iCVD process can also use plasma excitation to generate initiating free radicals. The can be done by flowing gas-phase monomer or by atomization of the liquid monomer species through a plasma field. This can take place at a range of pressures from atmospheric pressure to low vacuum.

In one embodiment the bonding of the coating to the substrate can be enhanced using a photo-grafting procedure. A photosensitive type II initiator, such as benzophenone, is applied to the substrate either by dipping the substrate in a solution containing the initiator and then drying before placing the substrate in the reactor or by vaporizing the initiator and flowing it into the vacuum reactor equipment as described above. If the later method is employed, sufficient time should be allowed so as to saturate the surface of the substrate. The type II initiator-coated substrate may then be exposed to UV radiation for a period of time, usually five minutes or more. After this exposure, the monomer species is flowed into the reactor as described herein (e.g., Example 1). UV radiation may or may not be applied and the type II initiator may or may not be flowing into the reactor during this time. Polymer photo-grafting is described in more detail below.

As described herein, in certain embodiments, the depositions were first carried out on silicon wafers. Silicon wafers provide a reflective surface so that interferometry can be used to monitor the real-time growth of the film during deposition. Also, silicon is sufficiently transparent to infrared wavelengths so that Fourier transform infrared (FTIR) spectroscopy in normal transmission mode can be used to examine the chemical structure of the deposited films. Finally, the reflective surface also allows VASE to be carried to get the thickness, and thus the growth rate, of the deposited film in a non-destructive manner. Thus, depositions on silicon were carried out to optimize the coating's growth rate and chemical structure. Fabric substrates were coated once the deposition conditions were optimized on flat substrates. The fabric substrates were then used for antimicrobial testing as described herein.

One aspect of the present invention relates to a method of coating a surface with a polymer, comprising the step of depositing a polymer on a surface using chemical vapor deposition; wherein said polymer comprises a plurality of monomers represented by formula I or II or both:

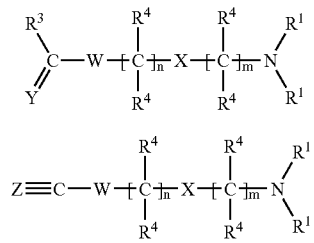

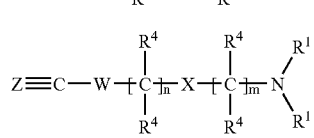

wherein, independently for each occurrence,

W is —C(=O)O—, —C(=O)N(R)—, —C(=O)S—, —C(R$^4$)$_2$—, —C(=O)—, —C(=NR)—, —C(=S)—, —C(R$^4$)=C(R$^4$)—, —C≡C—, -cycloalkyl-, -heterocycloalkyl-, -cycloalkenyl-, -heterocycloalkenyl-, -aryl-, or -heteroaryl-;

X is —O—, —N(R)—, —S—, —C(=O)O—, —C(=O)N(R)—, —C(=O)S—, —S(=O)—, —S(=O)$_2$—, —C(R$^4$)$_2$—, —C(=O)—, —C(=NR)—, —C(=S)—, —C(R$^4$)=C(R$^4$)—, —C≡C—, -cycloalkyl-, -heterocycloalkyl-, -cycloalkenyl-, -heterocycloalkenyl-, -aryl-, or -heteroaryl-;

Y is C(R$^2$)$_2$ or N(R$^2$); or Z is C(R$^2$) or N;

R is -hydrogen, -halogen, -alkyl, -cycloalkyl, -heterocycloalkyl, -alkenyl, -cycloalkenyl, -heterocycloalkenyl, -alkynyl, -cyano, -aryl, or -heteroaryl;

R$^1$ is -hydrogen, -halogen, -alkyl, -cycloalkyl, -heterocycloalkyl, -alkenyl, -cycloalkenyl, -heterocycloalkenyl, -alkynyl, -aryl, -heteroaryl or —[C(R)$_2$]$_p$—R;

R$^2$ is -hydrogen, -halogen, -alkyl, -cycloalkyl, -heterocycloalkyl, -alkenyl, -cycloalkenyl, -heterocycloalkenyl, -alkynyl, -aryl, -heteroaryl or —[C(R)$_2$]$_p$—R;

R$^3$ is -hydrogen, -halogen, -alkyl, -cycloalkyl, -heterocycloalkyl, -alkenyl, -cycloalkenyl, -heterocycloalkenyl, -alkynyl, -aryl, -heteroaryl or —[C(R)$_2$]$_p$—R;

R$^4$ is -hydrogen, -halogen, -alkyl, -cycloalkyl, -heterocycloalkyl, -alkenyl, -cycloalkenyl, -heterocycloalkenyl, -alkynyl, -aryl, -heteroaryl or —[C(R)$_2$]$_p$—R;

m is 0-7 inclusive;
n is 0-7 inclusive; and
p is 0-10 inclusive.

In certain embodiments, the present invention relates to the aforementioned method, wherein Y is C(R$^2$)$_2$ or Z is C(R$^2$).

In certain embodiments, the present invention relates to the aforementioned method, wherein Y is CH$_2$ or Z is CH.

In certain embodiments, the present invention relates to the aforementioned method, wherein R$^3$ is -hydrogen or -alkyl.

In certain embodiments, the present invention relates to the aforementioned method, wherein R$^3$ is -hydrogen or -methyl.

In certain embodiments, the present invention relates to the aforementioned method, wherein R$^1$ is -alkyl.

In certain embodiments, the present invention relates to the aforementioned method, wherein R$^1$ is -methyl.

In certain embodiments, the present invention relates to the aforementioned method, wherein X is —C(R$^4$)$_2$—.

In certain embodiments, the present invention relates to the aforementioned method, wherein R$^4$ is hydrogen.

In certain embodiments, the present invention relates to the aforementioned method, wherein X is —C(R$^4$)$_2$—; and R$^4$ is -hydrogen.

In certain embodiments, the present invention relates to the aforementioned method, wherein Y is CH$_2$ or Z is CH; R$^3$ is -hydrogen or -methyl; R$^1$ is -methyl; X is —C(R$^4$)$_2$—; and R$^4$ is -hydrogen.

Another aspect of the present invention relates to a method of coating a surface with a polymer, comprising the step of depositing a polymer on a surface using chemical vapor deposition; wherein said polymer comprises a plurality of monomers represented by formula III:

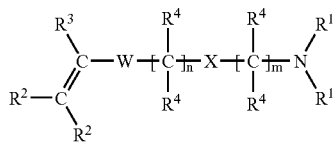

wherein, independently for each occurrence, W is

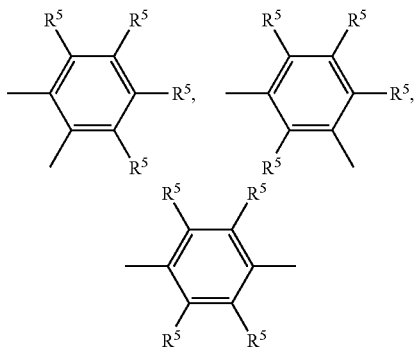

or —C(=O)O—;

X is —O—, —N(R)—, —S—, —C(=O)O—, —C(=O)N(R)—, —C(=O)S—, —S(=O)—, —S(=O)$_2$—, —C(R$^4$)$_2$—, —C(=O)—, —C(=NR)—, —C(=S)—, —C(R$^4$)=C(R$^4$)—, —C≡C—, -cycloalkyl-, -heterocycloalkyl-, -cycloalkenyl-, -heterocycloalkenyl-, -aryl-, or -heteroaryl-;

R is -hydrogen, -halogen, -alkyl, -cycloalkyl, -heterocycloalkyl, -alkenyl, -cycloalkenyl, -heterocycloalkenyl, -alkynyl, -cyano, -aryl, or -heteroaryl;

R$^1$ is -hydrogen, -halogen, -alkyl, -cycloalkyl, -heterocycloalkyl, -alkenyl, -cycloalkenyl, -heterocycloalkenyl, -alkynyl, -aryl, -heteroaryl or —[C(R)$_2$]$_p$—R;

R$^2$ is -hydrogen, -halogen, -alkyl, -cycloalkyl, -heterocycloalkyl, -alkenyl, -cycloalkenyl, -heterocycloalkenyl, -alkynyl, -aryl, -heteroaryl or —[C(R)$_2$]$_p$—R;

R$^3$ is -hydrogen, -halogen, -alkyl, -cycloalkyl, -heterocycloalkyl, -alkenyl, -cycloalkenyl, -heterocycloalkenyl, -alkynyl, -aryl, -heteroaryl or —[C(R)$_2$]$_p$—R;

R$^4$ is -hydrogen, -halogen, -alkyl, -cycloalkyl, -heterocycloalkyl, -alkenyl, -cycloalkenyl, -heterocycloalkenyl, -alkynyl, -aryl, -heteroaryl or —[C(R)$_2$]$_p$—R;

R$^5$ is -hydrogen, -halogen, -alkyl, -cycloalkyl, -heterocycloalkyl, -alkenyl, -cycloalkenyl, -heterocycloalkenyl, -alkynyl, -aryl, -heteroaryl or —[C(R)$_2$]$_p$—R;

m is 0-4 inclusive;
n is 0-4 inclusive; and
p is 0-10 inclusive.

In certain embodiments, the present invention relates to the aforementioned method, wherein n is 0.

In certain embodiments, the present invention relates to the aforementioned method, wherein n is 1.

In certain embodiments, the present invention relates to the aforementioned method, wherein n is 2.

In certain embodiments, the present invention relates to the aforementioned method, wherein n is 3.

In certain embodiments, the present invention relates to the aforementioned method, wherein n is 4.

In certain embodiments, the present invention relates to the aforementioned method, wherein m is 0.

In certain embodiments, the present invention relates to the aforementioned method, wherein m is 1.

In certain embodiments, the present invention relates to the aforementioned method, wherein m is 2.

In certain embodiments, the present invention relates to the aforementioned method, wherein m is 3.

In certain embodiments, the present invention relates to the aforementioned method, wherein m is 4.

In certain embodiments, the present invention relates to the aforementioned method, wherein W is

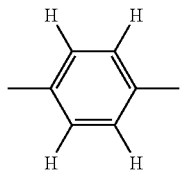

or —C(=O)O—.

In certain embodiments, the present invention relates to the aforementioned method, wherein $R^1$ is -alkyl.

In certain embodiments, the present invention relates to the aforementioned method, wherein $R^1$ is -methyl or -ethyl.

In certain embodiments, the present invention relates to the aforementioned method, wherein $R^2$ is -hydrogen or -alkyl.

In certain embodiments, the present invention relates to the aforementioned method, wherein $R^2$ is -hydrogen or -methyl.

In certain embodiments, the present invention relates to the aforementioned method, wherein $R^3$ is -hydrogen.

In certain embodiments, the present invention relates to the aforementioned method, wherein $R^4$ is -hydrogen.

In certain embodiments, the present invention relates to the aforementioned method, wherein W is

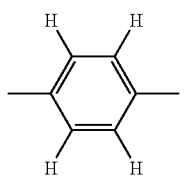

or —C(=O)O—; and $R^3$ is -hydrogen.

In certain embodiments, the present invention relates to the aforementioned method, wherein W is

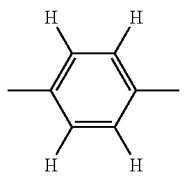

or —C(=O)O—; $R^3$ is -hydrogen; and $R^2$ is -hydrogen or methyl.

In certain embodiments, the present invention relates to the aforementioned method, wherein W is

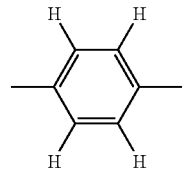

or —C(=O)O—; $R^3$ is -hydrogen; and $R^2$ is -hydrogen or methyl; and $R^1$ is alkyl.

In certain embodiments, the present invention relates to the aforementioned method, wherein W is

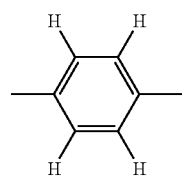

or —C(=O)O—; $R^3$ is -hydrogen; and $R^2$ is -hydrogen or methyl; $R^1$ is alkyl; X is —C($R^4$)$_2$—; and $R^4$ is -hydrogen.

In certain embodiments, the present invention relates to the aforementioned method, wherein W is

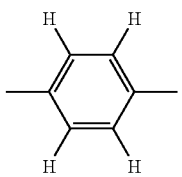

$R^3$ is -hydrogen; and $R^2$ is -hydrogen; $R^1$ is methyl; X is —C($R^4$)$_2$—; $R^4$ is -hydrogen; m is 0; and n is 0.

In certain embodiments, the present invention relates to the aforementioned method, wherein W is —C(=O)O—; $R^3$ is -hydrogen; and $R^2$ is -methyl; $R^1$ is ethyl; X is —C($R^4$)$_2$—; $R^4$ is -hydrogen; m is 1; and n is 0.

Another aspect of the present invention relates to a method of coating a surface with a polymer, comprising the step of depositing a polymer on a surface using chemical vapor deposition; wherein said polymer coating comprises a plurality of monomers selected from the group consisting of styrenes and acrylates.

Another aspect of the present invention relates to a method of coating a surface with a polymer, comprising the step of depositing a polymer on a surface using chemical vapor deposition; wherein said polymer coating comprises a plurality of monomers selected from the group consisting of (dimethylaminomethyl)styrene, (dimethylaminoethyl)styrene, (diethylaminomethyl)styrene, (diethylaminoethyl)styrene, (dimethylaminomethyl)-α-methylstyrene, (diethylaminoethyl)acrylate, (dimethylaminoethyl)acrylate, (diethylaminomethyl)acrylate, (dimethylaminomethyl)acrylate, (dimethylaminopropyl)acrylate, (diethylaminoethyl)methacrylate, (dimethylaminoethyl)methacrylate, (diethylaminomethyl)methacrylate, (dimethylaminomethyl)methacrylate and (dimethylaminopropyl)methacrylate.

In certain embodiments, the present invention relates to the aforementioned method, wherein said plurality of monomers is selected from the group consisting of (dimethylaminomethyl)styrene and (diethylaminoethyl)acrylate.

In certain embodiments, the present invention relates to the aforementioned method, wherein said polymer coating has a thickness of less than about 500 µg/cm$^2$.

In certain embodiments, the present invention relates to the aforementioned method, wherein said polymer coating has a thickness of less than about 100 µg/cm$^2$.

In certain embodiments, the present invention relates to the aforementioned method, wherein said polymer coating has a thickness of less than about 50 µg/cm$^2$.

In certain embodiments, the present invention relates to the aforementioned method, wherein said polymer coating has a thickness of less than about 10 µg/cm$^2$.

In certain embodiments, the present invention relates to the aforementioned method, wherein said polymer coating has a thickness of less than about 5 µg/cm$^2$.

In certain embodiments, the present invention relates to the aforementioned method, wherein said polymer coating is covalently bound to the surface.

In certain embodiments, the present invention relates to the aforementioned method, wherein said surface is selected from the group consisting of nylon, polyester, polyurethane, polyanhydride, polyorthoester, polyacrylonitrile, polyphenazine, latex, teflon, dacron, acrylate polymer, chlorinated rubber, fluoropolymer, polyamide resin, vinyl resin, Gore-tex®, Marlex®, expanded polytetrafluoroethylene (e-PTFE), low density polyethylene (LDPE), high density polyethylene (HDPE), polypropylene (PP), and poly(ethylene terephthalate) (PET).

In certain embodiments, the present invention relates to the aforementioned method, wherein said surface is rendered bactericidal to Gram-positive bacteria.

In certain embodiments, the present invention relates to the aforementioned method, wherein said surface is rendered bactericidal to Gram-negative bacteria.

In certain embodiments, the present invention relates to the aforementioned method, further comprising the step of adding an initiator.

In certain embodiments, the present invention relates to the aforementioned method, wherein said initiator is selected from the group consisting of dialkyl peroxides, hydroperoxides, diacyl peroxides, peresters, organic polyoxides, azo-compounds, and ketones.

In certain embodiments, the present invention relates to the aforementioned method, wherein said initiator is selected from the group consisting of t-amylperoxide, t-butylperoxide, 2,2'-azobis(2-methylpropane), benzophenone and diacetyl.

In certain embodiments, the present invention relates to the aforementioned method, wherein said surface is the surface of a medical device.

In certain embodiments, the present invention relates to the aforementioned method, wherein said surface is the surface of a medical device; and said medical device is selected from the group consisting of pins, screws, plates, ventriculoatrial shunts, ventriculoperitoneal shunts, dialysis shunts, heart valves, pacemakers, infuision pumps, vascular grafting prostheses, stents, sutures, surgical meshes, replacement prostheses, breast implants, tissue expanders, contact lenses, stoma appliances, artificial larynx, endotracheal tubes, tracheal tubes, gastrostomy tubes, biliary drainage tubes, biliary stents, catheters, bandages, adhesive tapes, and clear plastic adherent sheets.

Grafting

Figure 7:
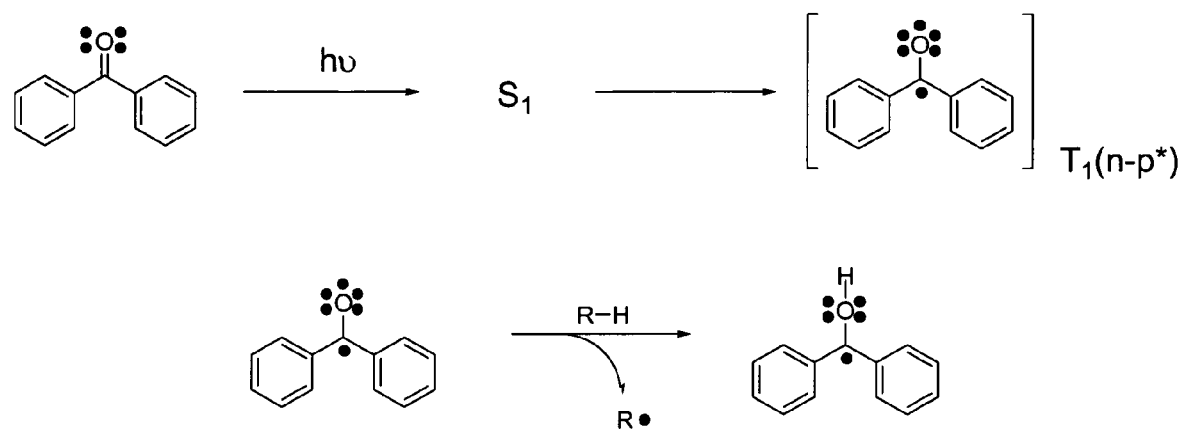
FIG. 7 depicts hydrogen abstraction by benzophenone through photochemical excitation.

Type-II photoinitiators are widely-used for grafting polymer chains to surfaces. Allen, N. S. *Photopolymerisation and Photoimaging Science and Technology*; Elsevier Applied Science: London, 1989; Roffey, C. G. *Photopolymerization of Surface Coatings*; Wiley: New York, 1982; Belfield, K.; Crivello, J. V. *Photoinitiated Polymerization*; American Chemical Society: Washington, D.C., 2003; and Fouassier, J.-P. *Photoinitiation, Photopolymerization, and Photocuring: Fundamentals and Applications; Hanser*: Munich, 1995. They work by abstracting labile hydrogen atoms from other molecules to create radicals. Benzophenone (BP) is one of such initiators and is able to abstract hydrogen atoms when excited photochemically. As shown in FIG. 7, BP, under UV irradiation, is excited to a singlet state ($S_1$) and then converted to a triplet state ($T_1$) by intersystem crossing (ISC). ISC progresses efficiently for BP due to the closeness of the energy levels of the $S_1$ and the $T_1$ states and occurs within a fraction of a second. The resulting $T_1$ state is long-lived, so there is ample time for the molecule to collide with and abstract a hydrogen atom from a donor molecule. This abstraction event leads to the production of two radicals, the benzohydrophenone radical and the donor radical, denoted R in FIG. 7. While both of these radicals can initiate polymerization, the donor radical is more efficient because it is less sterically hindered. In addition, the benzohydrophenone radical is less reactive because of the stabilizing effect of the two phenyl rings.

Grafting occurs when the donor molecule is part of a surface. When a hydrogen atom is abstracted from the surface, the resulting radical can initiate polymerization, leading to a covalently-attached polymer chain. Many chains will be grafted when a number of hydrogen atoms are abstracted from the surface. This grafting of chains onto the surface effectively creates a polymer film that is chemically bonded to the underlying material. Although grafted, the polymer layer has similar properties as a non-grafted thin film of the same material. At the same time, the chemical bonding between the two layers of materials offers many advantages. First, the grafted layer is resistant to abrasion. A covalent bond would have to be broken for a chain to be removed from the surface. Second, the grafted polymer is stable against virtually any solvent, provided that the solvent does not dissolve the underlying layer or cause bond-breaking reaction(s). This stability allows the surface to be used in solvents that would otherwise dissolve the bulk polymer.

Grafting using BP has been investigated by a number of researchers. Their methods can be divided into three main categories shown in Table 1. The most prominent is the all-solution-phase technique—both BP and the monomer are dissolved in a solution in which the surface to be grafted is immersed. On the other hand, a BP-pretreated surface can be exposed to vaporized monomer to effect grafting. This pretreatment can be wet or dry. In the wet case, BP is dissolved in a solution (typically acetone) and cast onto the surface to be grafted. The surface is then vacuum-dried to remove the solvent, leaving behind BP. The all-dry method exposes the to-be-grafted surface to BP vapor, and the surface uptakes BP during the exposure. Although different, these three categories use the same Type-II behavior of BP under UV irradiation—it abstracts labile hydrogen atoms from the surface to create chain-initiating radicals.

TABLE 1

Different Techniques of Using Benzophenone as a Photoinitiator

| Technique | Benzophenone delivery | Monomer delivery |
| --- | --- | --- |
| Wet | Solution-phase | Solution-phase |
| Semi-dry | Solution-phase | Vapor-phase |
| All-dry | Vapor-phase | Vapor-phase |

As with thin-film deposition, dry techniques, such as chemical vapor deposition (CVD), are becoming increasingly prevalent due to their environmental benefits. The success of all-dry CVD has been demonstrated by methods such as plasma-enhanced CVD (PECVD), hot-filament CVD (HFCVD), and initiated CVD (iCVD). Hollahan, J. R.; Bell, A. T. *Techniques and Applications of Plasma Chemistry*; Wiley: New York, 1974; Yasuda, H. *Plasma Polymerization; Academic*: Orlando, Fla., 1985; Inagaki, N. *Plasma Surface Modification and Plasma Polymerization*; Technomic: Lancaster, Pa., 1996; Lau, K. K. S.; Gleason, K. K. *J. Fluor. Chem.* 2000, 104, 119; Pryce Lewis, H. G.; Casserly, T. B.; Gleason, K. K. *J. Electrochem. Soc.* 2001, 148, F212; Loo, L. S.; Gleason, K. K. *Electrochem. Solid State Lett.* 2001, 4, G81; Pryce Lewis, H. G.; Caulfield, J. A.; Gleason, K. K. *Langmuir* 2001, 17, 7652; Murthy, S. K.; Olsen, B. D.; Gleason, K. K. *Langmuir* 2002, 18, 6424; and Mao, Y.; Gleason, K. K. *Langmuir* 2004, 20, 2484. A wide variety of polymeric and organosilicon materials have been made using these methods. iCVD, unlike PECVD and HFCVD, uses initiators to accelerate film growth and allow control of molecular weight and morphology, yet linear, well-defined chemical structures are produced. CVD is able to produce films of nanoscale thickness with macroscale uniformity on complex geometries. Pierson, H. O. *Handbook of Chemical Vapor Deposition*, 2nd ed.; Noyes Publications: Norwich, N.Y., 1999. The dryness of the process avoids the wetting and surface-tension effects associated with wet techniques, so surfaces with nano- or microscale topography can be coated uniformly. The added benefits of grafting motivate the investigation of an iCVD-like grafting process. The envisioned scheme combines the benefits of iCVD and grafting by exposing surfaces to vapors of a Type-II photoinitiator, such as BP, and a monomer in a continuous or a semi-batch manner. Although all-dry vapor-phase photografting has been examined, there have been few if any reports of one-step CVD-like grafting processes. Howard, G. J.; Kim, S. R.; Peters, R. H. *J. Soc. Dyers Colour.* 1969, 85, 468.; and Seiber, R. P.; Needles, H. L. *J. Appl. Polym. Sci.* 1975, 19, 2187. In one embodiment, this work uses an existing CVD chamber to perform solventless grafting, hereby referred to as grafting CVD (gCVD).

Postulated Mechanism of Attacking Bacteria

The antimicrobial coatings described herein and soluble cationic antimicrobials probably share a similar mechanism of attacking bacteria. Polycations, such as polymyxin B and antimicrobial cationic peptides of animals, displace the divalent cations that hold together the negatively charged surface of the lipopolysaccharide network, thereby disrupting the outer membrane of Gram-negative bacteria like *P. aeruginosa* and *E. coli*. Vaara, M. *Microbiol Rev.* 1992, 56, 395-411. This in itself might be sufficient for a lethal outcome. It is also possible that, having destroyed the outer membrane permeability barrier, the cationic groups of the tethered polymers further penetrate into the inner membrane, producing leakage. Such "self-promoted penetration" with the subsequent damage of the inner membrane has been described for polymyxin. The action of immobilized polycations against the Gram-positive bacteria *S. aureus* and *S. epidermidis* probably requires penetration of the cationic groups across the thick cell wall to reach the cytoplasmic membrane. Bactericidal action of amphipathic cationic antiseptics, such as benzalkonium chloride or biguanidine chlorhexidine, against Gram-positive bacteria is due primarily to the disruption of the cytoplasmic membrane. Denton, G. W. (2001) in *Disinfection, Sterilization, and Preservation*, ed. Block, S. S.; Lippincott Williams & Wilkins, Philadelphia. The cell wall of *S. aureus* is some 30 nm thick; therefore, portions of the antimicrobial films of the instant invention could penetrate the cell wall. Friedrich, C. L. et al. *Antimicrob. Agents Chemother.* 2000, 44, 2086-2092.

EXEMPLIFICATION

The invention now being generally described, it will be more readily understood by reference to the following examples, which are included merely for purposes of illustration of certain aspects and embodiments of the present invention, and are not intended to limit the invention.

Example 1

Polymer Deposition and Antimicrobial Testing

Films were deposited on 100-mm diameter silicon substrates in a custom-built vacuum reactor (Sharon Vacuum). The reactor was cylindrical with a height of 3.3 cm and a radius of 12 cm. The inlet of precursor gases and the exhaust were at opposite ends of the reactor. The top of the reactor was covered by a quartz plate (about 15 cm radius and about 2.5 cm thick), allowing visual inspection and laser interferometry. The reactor was equipped with a hot-filament array, which provided thermal energy for excitation of molecules. The array consisted of filaments spaced 15 mm apart. The clearance between the filaments and the stage was 23 mm. The substrate, either fabric or a 100 mm diameter silicon wafer, was placed on a backside-cooled stage (43° C.). The tungsten filaments (AWG 26, Omega Engineering) were resistively heated by applying a DC or AC voltage to 330° C., as measured by a thermocouple (Type K, AWG 36, Omega Engineering) directly attached to one of them. The reactor pressure was maintained at 200 mTorr with a throttling butterfly valve (MDC). In the case of fabric substrates, the deposition was carried out for an equal amount of time on each side of the fabric. The total deposition time was varied to achieve the desired coating thickness.

The monomer (dimethylaminomethyl)styrene (DMAMS) (95.0%+, MP Dajac) was vacuum purified before use and the initiator di-tert-amylperoxide (TAP) (98%, Aldrich) was used without further purification. DMAMS liquids were vaporized in a glass jar that was maintained at 80 ±1° C., respectively. DMAMS vapor was metered into the reactor through a mass-flow controller (1153, MKS). TAP was maintained at room temperature in a glass jar, and its vapor was also metered into the reactor through a mass flow controller (1479A, MKS). All vapors were mixed together before entering the reactor through a side port. Depositions on silicon wafers were monitored using an interferometry system equipped with a 633-nm HeNe laser source (JDS Uniphase). The cycle thickness was calculated by dividing the actual thickness, as measured using variable-angle spectroscopic ellipsometry (VASE), by the number of cycles. VASE was performed on a J. A. Woollam M-2000 spectroscopic ellipsometer with a xenon light source. Data were acquired at three angles (65°, 700, and 75°) and 225 wavelengths, and the Cauchy-Urbach model was used to fit the data. Fourier transform infrared (FTIR) spectroscopic measurements were performed on a Nicolet Nexus 870 ESP spectrometer in normal transmission mode using a DTGS KBr detector over the range of 400 to 4000 cm$^{-1}$ at a 4 cm$^{-1}$ resolution averaged over 64 scans. As a comparison, a PMMA standard (Alfa Aesar) was dissolved in tetrahydrofuran, and the solution was cast onto a silicon wafer.

Depositions on fabric were monitored by weighing the sample before and after deposition on a Mettler-Toledo XS205 Dual Range balance. Some fabric coatings were imaged using a Jeol scanning electron microscope after sputtering conductive layer of gold. Antimicrobial testing of coated fabric substrates was carried out according to ASTM E2149-01 "Standard Test Method for Determining the Antimicrobial Activity of Immobilized Antimicrobial Agents Under Dynamic Contact Conditions." In general, the microbe tested was cultured overnight in the appropriate culture medium (i.e., LB medium for *E. coli*). A few milliliters of the culture were placed in phosphate buffered saline. This solution was split into 50 ml into 250 ml sterile Erlenmeyer flasks, one flask per sample to test and one for a control sample of uncoated fabric. The sample was swirled at 200 rpm for a set period of time, usually one hour. The initial and post-test viable cell concentrations were measured by the serial dilution-plate count method. Both mass series and time series tests have been carried out against *E. coli*.

Example 2

Polymer Deposition Results

Depositions of poly(dimethylaminomethylstyrene) (PDMAMS) were carried out to optimize the growth rate and chemical structure of the polymer prior to depositions on fabric and antimicrobial testing. The filament temperature and the substrate temperature were both optimized at a reactor pressure of 200 mTorr, DMAMS flow rate of 2.4 sccm, t-amylperoxide flow of 0.4 sccm and a polished silicon wafer substrate. It is noted that the commercially available DMAMS monomer is a 50/50 mixture of the ortho and para isomers. As can be seen from the chart, the optimal conditions to maximize growth were at a filament temperature of 604 K and a substrate temperature of 320 K, which resulted in a growth rate of 106 Angstroms/min. Higher filament temperatures did not result in a further increase in deposition rate (data not shown). Increasing the pressure or decreasing the substrate temperature resulted in monomer condensation to form liquid on the substrate and therefore a low quality film was deposited. The precursor flow rates are the nominal maximum flow rate achieved with the current system design and equipment, but could be increased by altering equipment.

Figure 8:
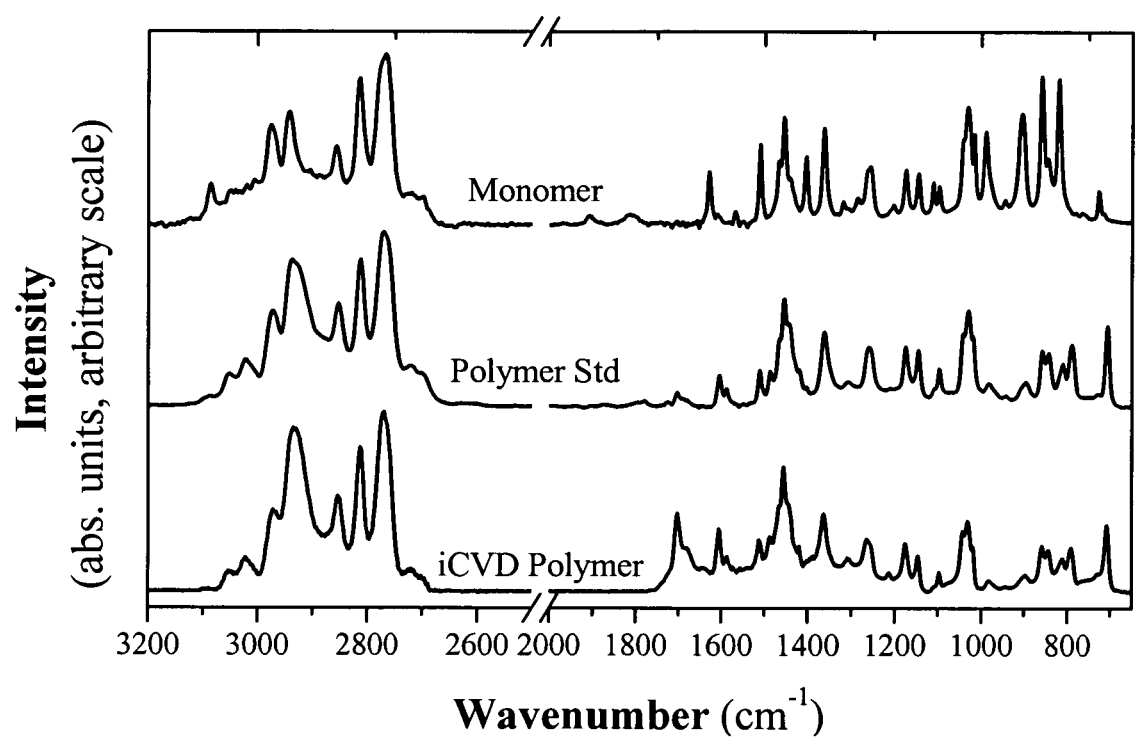
FIG. 8 depicts FTIR spectra for DMAMS monomer, commercially available polymer and the iCVD polymer (arbitrary scale).

The chemical structure of the deposited PDMAMS polymer film was confirmed using Fourier transform infrared (FTIR) spectroscopy. These results are presented in FIG. 8. Note that the scales of the three spectra are different and the chart is for qualitative comparison only. The iCVD polymer was deposited at the optimal growth rate conditions described above. The spectra for the polymer standard and the iCVD polymer are nearly identical with marked difference between these and the monomer spectrum. The only significant difference between the polymer spectra is the peak at 1700 wavenumber in the iCVD polymer spectrum. This peak can be attributed to the presence of un-terminated chains that form carbonyl species upon exposure to oxygen. Therefore, the deposition process results in substantially the same material as formed using conventional solution polymerization.

It should be noted as well that the deposited polymer was not soluble in THF, DMF, a number of other organic solvents, or water. The commercially available polymer is soluble in organic solvents such as THF and is sparingly soluble (50 ppm) in water. Therefore, the iCVD polymer may be crosslinked during deposition through an unknown mechanism. This is likely an advantage for the application under study as the durability of the coating should increase with some degree of crosslinking. The molecular weight of the deposited polymer could not be determined due to the insolubility in organic solvents.

Figure 9:
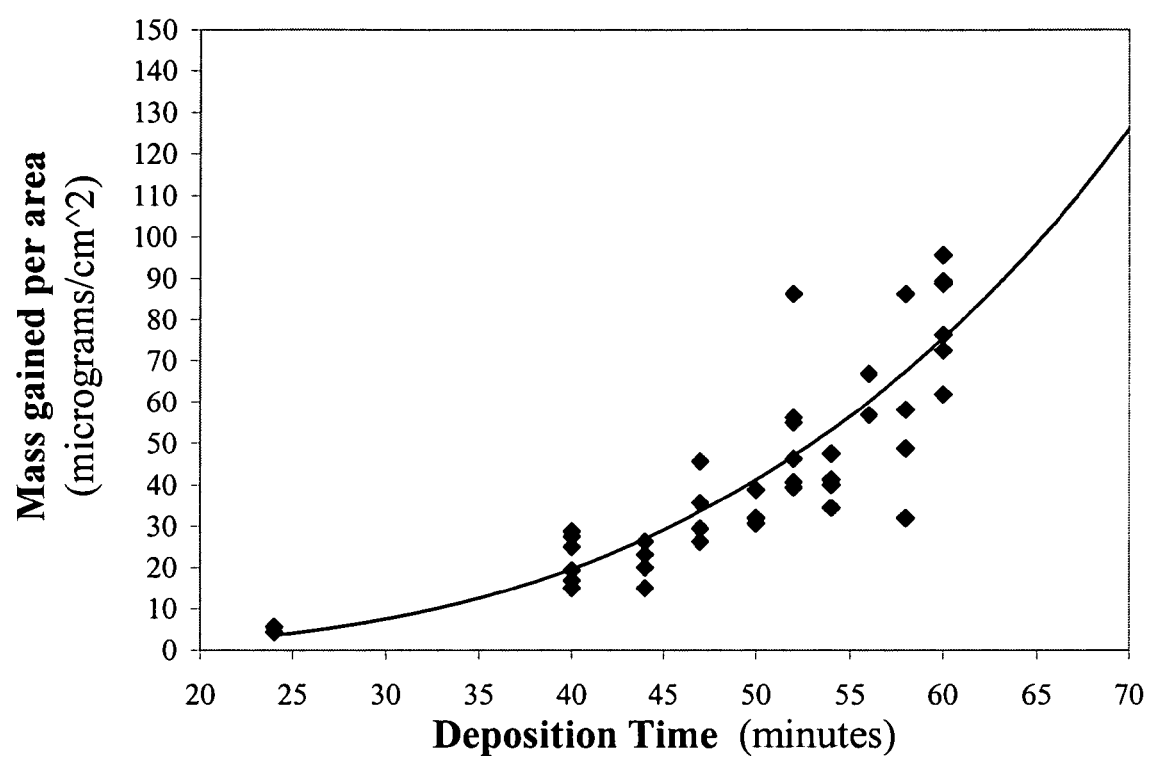
FIG. 9 depicts mass gained per area for PDMAMS on dyed nylon fabric as a function of deposition time.
Figure 10:
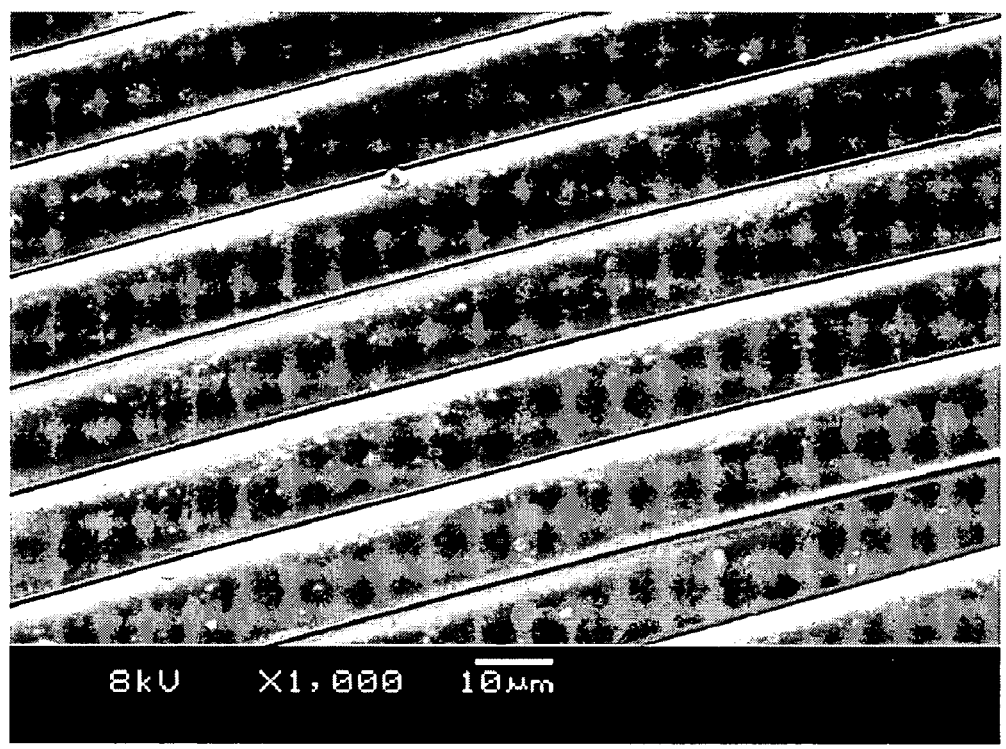
FIG. 10 depicts an SEM image of uncoated nylon fabric.
Figure 11:
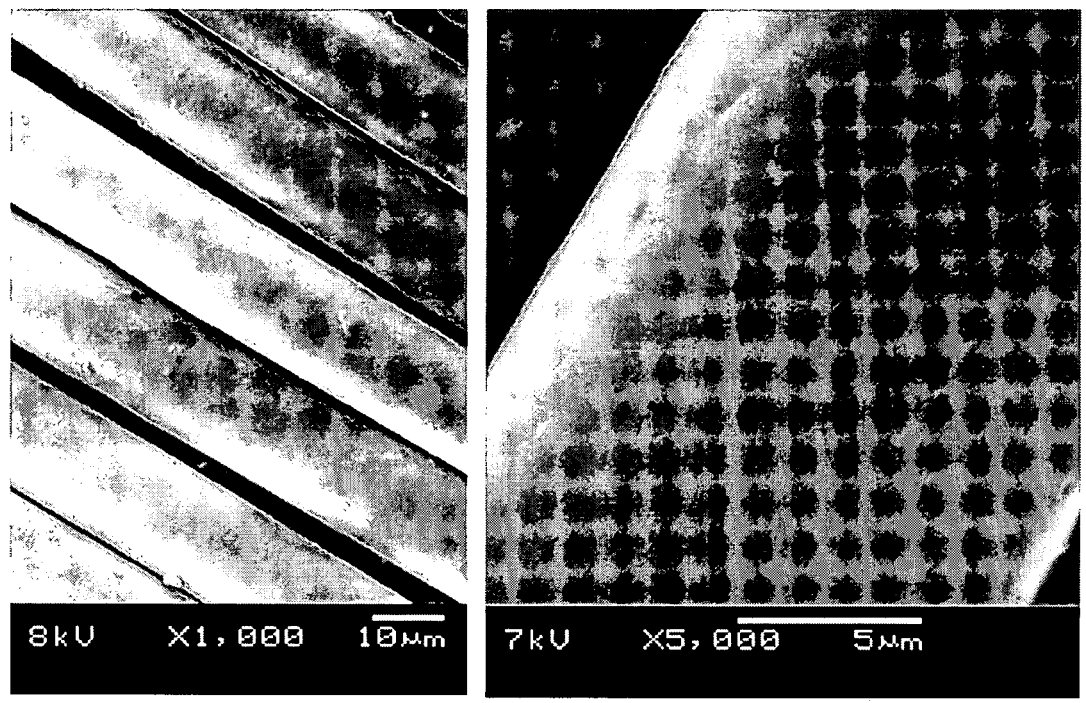
FIG. 11 depicts SEM images of nylon fabric coated with 86 µg/cm$^2$ of PDMAMS.

The deposition rate of PDMAMS on fabric was determined by weighing the sample before and after deposition to determine the mass gained during the process. The conditions employed were the optimized growth conditions described above. The deposition time was varied to vary the amount of coating applied to the fabric. A deposition was done for half the time, and then the sample was flipped over and coated for the same amount of time to ensure an even coating on both sides of the fabric. The total deposition time and mass gained per unit area of fabric are indicated on the chart shown in FIG. 9. The fabric substrates consisted of woven, dyed nylon from the shell of an Army Poncho Liner. The chart shows that the deposition rate on fabric is somewhat more erratic than on a flat substrate. The key factor in this variability is likely the temperature of the fabric. This more difficult to characterize and control than that of a silicon wafer, and yet, this is a critical factor in the film growth rate. The fabric temperature may vary due to changes in thermal contact between the fabric and the cooling stage from sample to sample. It was attempted to hold the fabric at 320 K, but this could not be accurately measured. The basis weight of the fabric was approximately 5 mg/cm$^2$ and the average fiber diameter was 14 µm. FIGS. 10 and 11 show scanning electron microscope (SEM) images of the uncoated and coated fabric, respectively. As seen in FIG. 11, the coating forms a conformal layer on the fiber surface and does not occlude the pores of the fabric. Thus, the "breathability" of the fabric is not affected. While it is difficult to directly observe the thickness of the coating, it is possible to estimate the approximate coating thickness on the fiber surface. For instance, for the coating shown in FIG. 11, 86 µg/cm$^2$ of PDMAMS, the average fiber coating thickness is estimated at about 50 to about 60 nm.

Figure 12:
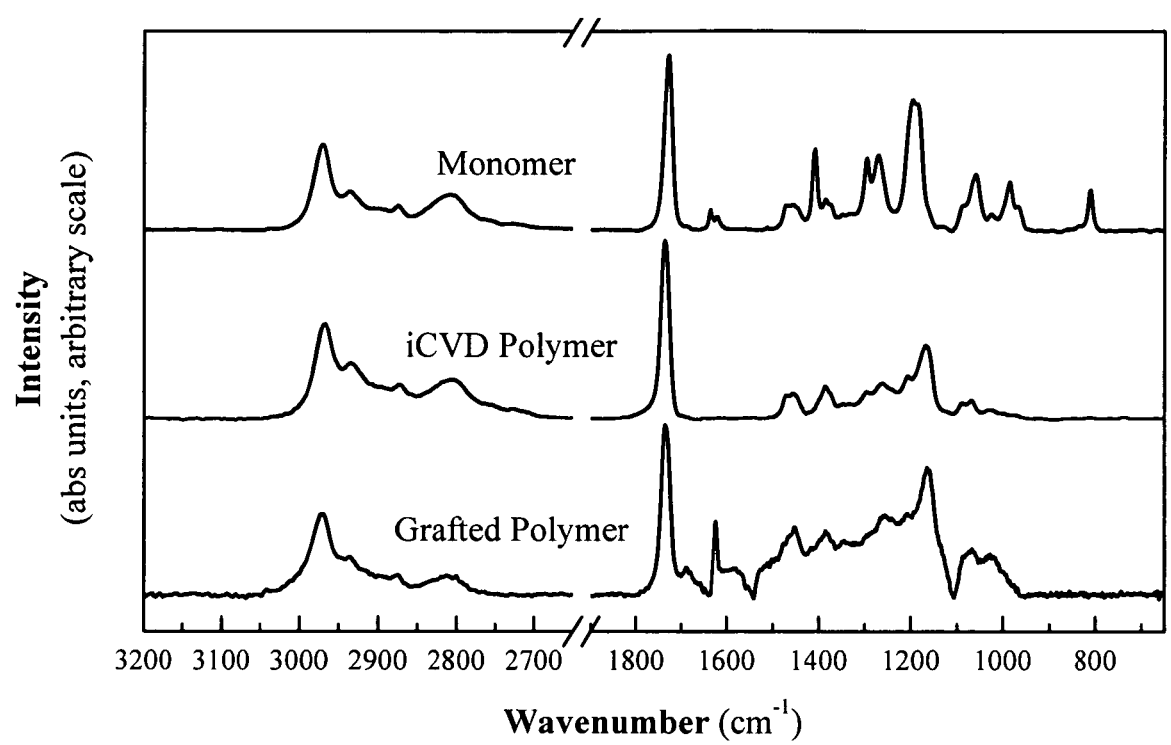
FIG. 12 depicts FTIR spectra for DEAEA monomer, the initiated CVD polymer, and the polymer grafted to spin-cast nylon (arbitrary scale). Nylon film was used as the background for the grafted polymer spectra; thus, none of the peaks is due to nylon.

The key factor for antimicrobial activity of the polymer is that the amino group has a pKa of greater than about 8.0 so that it is protonated in neutral solutions. There are many monomers other than DMAMS that satisfy this requirement. One of these, (diethylaminoethyl)acrylate (DEAEA), was also deposited by iCVD. However, the deposition was not as extensively characterized as that of DMAMS. Good quality films were grown at various conditions. One set of conditions wherein good films were obtained had a filament temperature of 604 K, substrate temperature of 305K, reactor pressure of 210 mTorr, DEAEA flow rate of 3.5 sccm, t-amylperoxide flow of 0.4 sccm for deposition on a polished silicon wafer substrate. This resulted in a growth rate of approximately 2000 A/min, nearly twenty times higher than the rate of PDMAMS deposition. The FTIR spectra of DEAEA and its iCVD polymer are shown in FIG. 12, along with the spectrum of PDEAEA grafted onto a nylon film, which is described in more detail below. Again, the spectra are plotted on different scales and the figure is useful for qualitative comparison only. The polymer was not commercially available, so there is no standard reference spectrum shown. There are several differences between the monomer and iCVD polymer spectra, but the key changes are the loss of the C=C doublet at 1640 and 1625 cm$^{-1}$ and the =CH$_2$ wag peak at 810 cm$^{-1}$. The loss of these peaks show that the iCVD process has formed the polymer and no monomer remains in the film.

Example 3

Grafting Results

As mentioned above, for some applications it may be advantageous to enhance the bonding of the antimicrobial coating to its substrate. To this end, a covalent polymer grafting scheme was devised. A type II photo initiator is used in conjunction with a UV source to enact grafting of the polymer to a surface. A type II photoinitiator is a photosensitive molecule that, when excited, abstracts a hydrogen from the substrate surface. This results in a radical on the surface which can initiate polymerization. The process is described in general in the detailed description. The specific conditions used for successful grafting of PDEAEA used in this work are described here. Nylon was spin cast onto a silicon wafer and the thickness was determined by variable angle spectroscopic ellipsometry and the FTIR spectrum of this layer was taken. Benzophenone (BP) was flowed into the reactor at 0.5 sccm and allowed to saturate the nylon film at approximately 250 mTorr. After some time, a broad spectrum UV lamp was turned on at 350 W for five minutes while BP was still flowing. At the end of this time, a flow of 6 sccm of DEAEA was begun while the UV lamp was on and BP was still flowing. The pressure was maintained at 400 mTorr. The deposition time was 5 minutes. Approximately 4000 Angstroms were deposited in this time. The film was then placed in a deionized water bath for 48 hrs. PDEAEA is highly soluble in water and any non-grafted polymer was removed over this time.

This process resulted in a grafted PDEAEA film with a thickness of 2000 Angstroms. While this work was done on flat substrate, presumably the same thickness could be achieved on fiber surfaces. As shown above, only 50-60 nm of film on the fiber surface were required to impart antimicrobial activity against both $E.$ $coli$ and $S.$ $epidermidis$, so therefore this grafting process should provide a coating of sufficient thickness in one step. The FTIR spectrum of the grafted polymer shown in FIG. 12 was taken after this 48 hr water bath with the spin cast nylon film used as the background. Thus, none of the peaks should be attributable to the nylon. While the spectrum does not exactly match that of the iCVD polymer, the main peaks are clearly visible. The entire C—H peak region at 3000-2800 cm$^{-1}$ appears nearly identical. There is a peak found near 1625 cm$^{-1}$, as in the monomer, but other monomer peaks are not visible, particularly the =CH$_2$ twist peak at 810 cm$^{-1}$. Thus, the peak at 1625 cm$^{-1}$, along with the broad shoulder from 1625 to 1550 cm$^{-1}$, probably does not indicate monomer remaining in the film. Any monomer that was deposited should have been removed in the 48 hr. water bath. The film was also annealed at 308 K for one hour in a nitrogen atmosphere, which should have removed any monomer remaining in the film. But, the spectrum did not change after this anneal. Instead, some other change is likely taking place in the deposited polymer or nylon films. Possibly, the nylon and/or PDEAEA films are UV sensitive. In addition, a control deposition was run in which no BP was used. A film of PDEAEA still formed in the presence of UV excitation, but the growth rate was very low, only 50 A/min, and the deposited film was rapidly and completely removed in a water bath. This shows that the type II photoinitiator is most likely initiating from the surface, which results in the film being covalently bonded to the surface and simultaneously increases the film deposition rate.

Example 4

Antimicrobial Results

The coated samples of fabric were tested using ASTM E2 149-01. The results of testing to date are presented in Table 2; test microbe A is $E.$ $Coli$ and test microbe B is $S.$ $Epidermidis$. The substrate used was the woven dyed nylon fabric of the shell of an Army Poncho Liner. In all cases the coating was poly(DMAMS). The starting concentration of viable bacteria as well results of a control test carried out simultaneously against an uncoated piece of the same fabric are included. A series of tests against $E.$ $coli$ (A) found that a coating of 39 µg/cm$^2$ was the minimum amount that resulted in a significant kill. A less extensive series of tests found that a coating of 86 µg/cm$^2$ worked in nine hours against $S.$ $epidermidis$ (B), but this is not necessarily the minimum coating or minimum time required to get significant bactericidal action. The percent reduction in viable $S.$ $epidermidis$ (and therefore the corresponding log of viable bacteria) was calculated as described in ASTM E2149-01 for tests in which the control concentration showed some significant change in viable bacteria concentration from the initial concentration. In such cases the reduction is determined vs. the control concentration instead of the initial concentration.

TABLE 2

Results of testing antimicrobial polymer coating on fabric against two microbes.

| Coating Weight (µg/cm$^2$) | Test Length (hr) | Test Microbe | Initial Microbe Concentration (CFU/ml) | Control Microbe Concentration (CFU/ml) | Final Microbe Concentration (CFU/ml) | % Reduction in Viable Bacteria | Log Reduction in Viable Bacteria |
|---|---|---|---|---|---|---|---|
| 39 | 1 | A | 8.7 × 10$^7$ | 8.0 × 10$^7$ | 23 | 99.99997% | 6.59 |
| 86 | 9 | B | 1.5 × 10$^7$ | 5.5 × 10$^6$ | 10 | 99.99993% | 6.17 |

Figure 4:
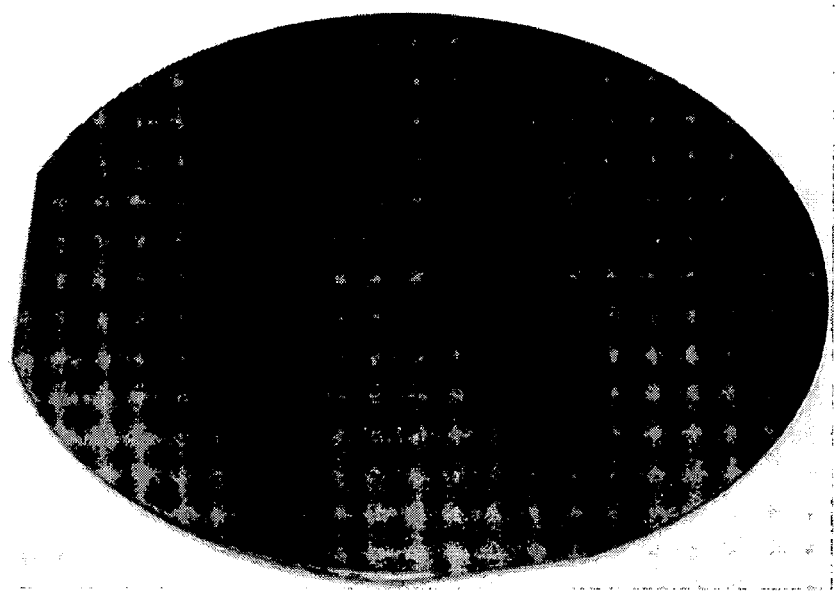
FIG. 4 depicts the results of a reactor design which allows one to deposit films in a combinatorial manner. This means that one can examine five filament temperatures during one deposition, resulting in the wafer image (A) and thickness map obtained by variable angle spectroscopic ellipsometry (B).
Figure 4:
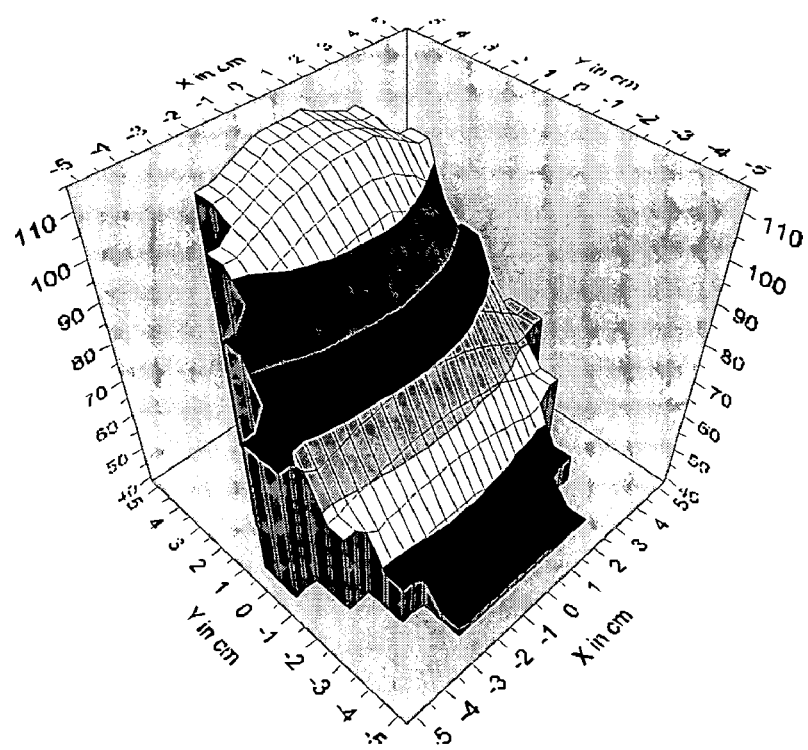

Further testing was done using the PDMAMS coating against $E.$ $coli$. Specifically, FIG. 4 shows a time series in which the test method was modified and samples of test solution were taken and tested at the indicated time. Again, this testing was done on a coated piece of the same fabric described above and coated with 39 µg/cm$^2$ of PDMAMS, which was the minimum effective amount. The results shown indicate a 99.99% reduction (4.0 log reduction) in two minutes and a continuing kill up to 99.99997% (6.6 log reduction) in one hour.

In addition, different techniques, materials and substrates were compared, as shown in the table below (Table 3).

TABLE 3

Comparison to Other Non-Leaching Antimicrobial Technologies.

| Technique - material - substrate | # Steps | Processing Time | % Kill** |
|---|---|---|---|
| ATRP - polyquaternary amine - glass/paper | 3 | 96 hrs | 99.85-99.97% |
| Silanol condensation - polyquaternary amine - fabric | 3 | ~45 min (estimated) | 93-99.5% |
| iCVD - poly tertiary amine - fabric | 1 | 40-50* min | 99.9999% |

Key:
*New monomer should reduced this to less than about 10 min;
**All examined effectiveness against *E. coli* using same standardized test (ASTM E2149), so results are directly comparable.

Incorporation by Reference

All of the patents and publications cited herein are hereby incorporated by reference. In addition U.S. application Ser. No. 10/513,880, filed Oct. 29, 2002; and U.S. application Ser. No. 10/282,905, filed May, 9, 2003 are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A polymer composition coated onto a surface of a substrate, wherein said polymer coating comprises a plurality of monomers represented by formula III:

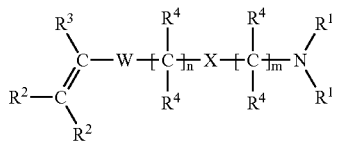

III wherein, independently for each occurrence,
W is

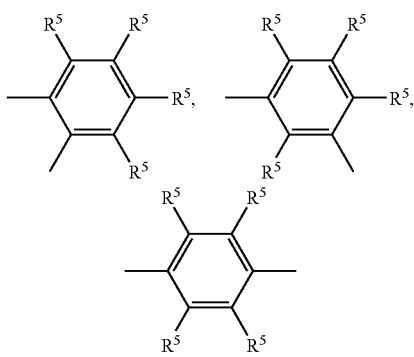

X is absent, —O—, —N(R)—, —S—, —C(═O)O—, —C(═O)N(R)—, —C(═O)S—, —S(═O)—, —S(═O)$_2$—, —C(R$^4$)$_2$—, —C(═NR)—, —C(═S)—, —C(R$^4$)═C(R$^4$)—, —C≡C—, -cycloalkyl-, -heterocycloalkyl-, -cycloalkenyl-, -heterocycloalkenyl-, -aryl-, or -heteroaryl-;

R is -hydrogen, -halogen, -alkyl, -cycloalkyl, -heterocycloalkyl, -alkenyl, -cycloalkenyl, -heterocycloalkenyl, -alkynyl, -cyano, -aryl, or -heteroaryl;

R$^1$ is -hydrogen, -halogen, -alkyl, -cycloalkyl, -heterocycloalkyl, -alkenyl, -cycloalkenyl, -heterocycloalkenyl, -alkynyl, -aryl, -heteroaryl or —[C(R)$_2$]$_p$—R;

R$^2$ is -hydrogen, -halogen, -alkyl, -cycloalkyl, -heterocycloalkyl, -alkenyl, -cycloalkenyl, -heterocycloalkenyl, -alkynyl, -aryl, -heteroaryl or R$^3$ is -hydrogen, -halogen, -alkyl, -cycloalkyl, -heterocycloalkyl, -alkenyl, -cycloalkenyl, -heterocycloalkenyl, -alkynyl, -aryl, -heteroaryl or —[C(R)$_2$]$_p$—R;

R$^4$ is -hydrogen, -halogen, -alkyl, -cycloalkyl, -heterocycloalkyl, -alkenyl, -cycloalkenyl, -heterocycloalkenyl, -alkynyl, -aryl, -heteroaryl or —[C(R)$_2$]$_p$—R;

R$^5$ is -hydrogen, -halogen, -alkyl, -cycloalkyl, -heterocycloalkyl, -alkenyl, -cycloalkenyl, -heterocycloalkenyl, -alkynyl, -aryl, -heteroaryl or —[C(R)$_2$]$_p$—R;

m is 0-4 inclusive;

n is 0-4 inclusive; and p is 0-10 inclusive.

2. The polymer composition coated onto a surface of a substrate of claim 1, wherein W is

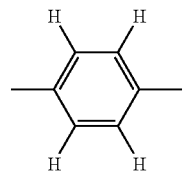

3. The polymer composition coated onto a surface of a substrate of claim 1, wherein R$^1$ is -methyl or -ethyl.

4. The polymer composition coated onto a surface of a substrate of claim 1, wherein R$^2$ is -hydrogen or -methyl.

5. The polymer composition coated onto a surface of a substrate of claim 1, wherein R$^3$ is -hydrogen.

6. The polymer composition coated onto a surface of a substrate of claim 1, wherein R$^4$ is -hydrogen.

7. The polymer composition coated onto a surface of a substrate of claim 1, wherein W is

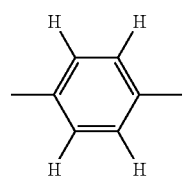

and R$^3$ is -hydrogen.

8. The polymer composition coated onto a surface of a substrate of claim 1, wherein W is

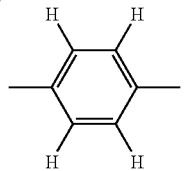

$R^3$ is -hydrogen; and $R^2$ is -hydrogen or -methyl.

9. The polymer composition coated onto a surface of a substrate of claim 1, wherein W is

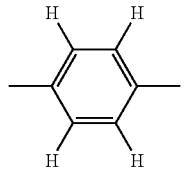

$R^3$ is -hydrogen; and $R^2$ is -hydrogen or -methyl; and $R^1$ is -alkyl.

10. The polymer composition coated onto a surface of a substrate of claim 1, wherein W is

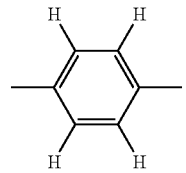

$R^3$ is -hydrogen; and $R^2$ is -hydrogen or -methyl; $R^1$ is -alkyl; X is —C($R^4$)$_2$—; and $R^4$ is -hydrogen.

11. The polymer composition coated onto a surface of a substrate of claim 1, wherein $R^1$ is -methyl.

* * * * *